US007322967B2

(12) United States Patent
Kondo

(10) Patent No.: US 7,322,967 B2
(45) Date of Patent: Jan. 29, 2008

(54) PANT-TYPE DISPOSABLE GARMENT

(75) Inventor: Masahiro Kondo, Kobe (JP)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 11/051,727

(22) Filed: Feb. 4, 2005

(65) Prior Publication Data

US 2005/0177124 A1   Aug. 11, 2005

Related U.S. Application Data

(60) Provisional application No. 60/543,171, filed on Feb. 10, 2004.

(51) Int. Cl.
*A61F 13/20* (2006.01)

(52) U.S. Cl. ............... 604/385.29; 604/395; 604/391; 604/389; 604/385.11; 604/385.3

(58) Field of Classification Search ........... 604/358.29, 604/385.28, 385.11, 392, 395, 391, 389, 385.3, 604/385.29
See application file for complete search history.

(56) References Cited

U.S. PATENT DOCUMENTS

| 972,288 | A | * | 10/1910 | Taylor | ........................ 604/397 |
|---|---|---|---|---|---|
| 2,564,094 | A | * | 8/1951 | Brandl | ........................ 604/392 |
| 4,022,212 | A | * | 5/1977 | Lovison | ..................... 604/395 |
| 4,637,078 | A | * | 1/1987 | Southwell | ..................... 2/408 |
| 4,835,795 | A | * | 6/1989 | Lonon | ........................... 2/408 |
| 4,988,346 | A | * | 1/1991 | Pfefferkorn | ................ 604/389 |
| 5,069,678 | A | * | 12/1991 | Yamamoto et al. | .... 604/385.21 |
| 5,445,628 | A | * | 8/1995 | Gipson et al. | ............... 604/392 |
| 6,102,899 | A | | 8/2000 | Yimin et al. | |
| 6,243,871 | B1 | * | 6/2001 | Fidler | ............................. 2/80 |
| 6,508,797 | B1 | * | 1/2003 | Pozniak et al. | ......... 604/385.11 |
| 6,540,730 | B1 | * | 4/2003 | Niedermeyer | .......... 604/385.27 |
| 6,605,071 | B1 | * | 8/2003 | Gray et al. | ............ 604/385.28 |
| 6,752,797 | B2 | * | 6/2004 | Oba | ............................ 604/395 |
| 2001/0041879 | A1 | * | 11/2001 | Karami et al. | ............... 604/386 |
| 2002/0138065 | A1 | * | 9/2002 | Yeater et al. | ................ 604/395 |

(Continued)

FOREIGN PATENT DOCUMENTS

EP        1133966        *  9/2001

OTHER PUBLICATIONS

PCT International Search Report dated Jul. 13, 2005.

*Primary Examiner*—Tatyana Zalukaeva
*Assistant Examiner*—Ginger Chapman
(74) *Attorney, Agent, or Firm*—Kevin C. Johnson; Roddy M. Bullock; Gary J. Foose

(57) ABSTRACT

A pant-type disposable garment having a waist opening and a pair of leg openings is disclosed. The garment comprises a first waist panel, a second waist panel and a crotch panel positioned between, the first waist panel and the second waist panel. The crotch panel is openable and reclosable with respect to at least the second waist panel. The garment further comprises a releasable joint and a fastening member. The releasable joint releasably joins the crotch panel to the second waist panel to preform a pant shape. The releasable joint is released to first open the crotch panel. The fastening member is capable of refastening the crotch panel to the second waist panel to reform the pant shape after the releasable joint is released.

12 Claims, 16 Drawing Sheets

U.S. PATENT DOCUMENTS

| | | |
|---|---|---|
| 2002/0151858 A1* | 10/2002 | Karami et al. ........... 604/385.3 |
| 2003/0220626 A1 | 11/2003 | Karami |
| 2005/0177125 A1* | 8/2005 | Kondo ................. 604/385.29 |
| 2006/0116654 A1* | 6/2006 | Kondo ....................... 604/395 |
| 2006/0259001 A1 | 11/2006 | Roehrl |

* cited by examiner

PANT-TYPE DISPOSABLE GARMENT

CROSS REFERENCE TO RELATED APPLICATION

This application claims the benefit of U.S. Provisional Application No. 60/543,171, filed Feb. 10, 2004.

FIELD OF THE INVENTION

The present invention relates to a pant-type disposable garment having a refastenable fastening system used for infants, adults or incontinent persons; or a pant-type disposable incontinent garment having a refastenable fastening system used with another absorbent article such as a supplemental inner pad.

BACKGROUND OF THE INVENTION

A disposable absorbent article worn to assist in the collection of bodily discharges of incontinent persons is well known in the art. Such a conventional art includes a pant-type disposable diaper in which the ventral and dorsal portions of the diaper are connected and fixed together at both side edges of the ventral and dorsal portions to form a pair of leg openings and a unitary waist opening. For example, U.S. Pat. No. 5,449,353 and U.S. Pat. No. 5,735,839 disclose such a conventional pant-type diaper. One drawback with such a pant-type diaper is that the manner of applying the diaper is limited to being pulled on like a pant. Applying the absorbent article like a pant is advantageous in many cases, and is particularly suited for active, walking incontinent persons. However, even for the same wearer, there may be time when it would be useful to apply the absorbent article like a conventional tape-type diaper. For example, it might be more convenient to apply the absorbent article like a tape-type diaper when there is a desire not to remove the wearer's shoes. Since it is difficult to know when a particular mode of applying the absorbent article will be needed, it is beneficial to have an absorbent article that is adaptable to being used both as a pant-type diaper and as a tape-type diaper. This is preferable to keeping both types of absorbent article available in advance. An absorbent article that can be applied both like a pant-type diaper and like a tape-type diaper also permits the interior of the absorbent article to be easily checked without pulling the article downward.

A typical example of such a convertible pant-type diaper is disclosed in, e.g., International Patent Publications WO 00/35398. It discloses a pant-type disposable diaper in which the front and rear waist regions of the diaper are releasably fastened to each other at the side-panel portions of the diaper which are positioned on the hips of the wearer when the diaper is worn. The diaper includes a refastenable fastening system disposed to the side panels of the diaper for fastening the front and rear waist regions to each other. Such a disposable diaper as disclosed in WO 00/35398 can be applied both like a pant-type diaper and like a tape-type diaper because of the refastenable fastening system typically comprising a hook-type fastener and a loop-type fastener releasably engaged with the hook-type fastener. Such releasable fastening as disclosed in the prior art is typically achieved by overlapping the side-panel portions of the front and rear waist regions with each other. The overlap of the side-panel portions of the front and rear waist regions forms undesirable bumps at the side-panel portions while the diaper is worn. Such an undesirable bump could easily trigger undesirable detachment of the overlapped side-panel portions from each other during use of the diaper, e.g., due to friction exerted between the diaper and the wearer's garment. Further, the side-panel portion of a convertible pant-type diaper is typically elasticized in the transverse direction of the diaper. Therefore, a user of such a conventional convertible pant-type diaper suffers from the drawback that it is difficult for the user to overlap the side-panel portions of the front and rear waist regions with each other. The drawback results from the fact that the transversely elongated side-panel portion tends to recover its original size/shape due to the elasticity of the side-panel portion.

Another type of a pant-type diaper is disclosed in European Patent Application EP1133966A2. It discloses a disposable pull-on diaper in which the crotch region of the diaper is openable and reclosable with respect to the front waist region of the diaper. The fastening member such as a mechanical fastener, an adhesive tape and the like is provided to refastenably join the crotch region to the front waist region to form a pant shape. The diaper formed into a pant shape is pulled on the wearer's body like a pant. However, the fastening member can unfasten due to the force exerted to the fastening member while pulling up the diaper on the wearer. When it happens, the user must refasten the fastening member to reform a pant shape of the diaper and repeat the application process of the diaper to the wearer's body. In a worse case, the fastening member may be damaged to get out of order.

Based on the foregoing, there is a need for a pant-type disposable garment in which the crotch portion is openable and reclosable, but does not unexpectedly open during the wearing process of the garment.

SUMMARY OF THE INVENTION

The present invention is directed to a pant-type disposable garment having a waist opening and a pair of leg openings. The garment comprises a first waist panel, a second waist panel and a crotch panel positioned between the first waist panel and the second waist panel. The crotch panel is openable and reclosable with respect to at least the second waist panel. The garment further comprises a releasable joint and a fastening member. The releasable joint releasably joins the crotch panel to the second waist panel to preform a pant shape. The releasable joint is released to first open the crotch panel. The fastening member is capable of refastening the crotch panel to the second waist panel to reform the pant shape after the releasable joint is released.

BRIEF DESCRIPTION OF THE DRAWINGS

While the Specification concludes with claims which particularly point out and distinctly claim the invention, it is believed the present invention will be better understood from the following description of preferred embodiments taken in conjunction with the accompanying drawings, in which like reference numerals identify identical elements and wherein:

DETAILED DESCRIPTION OF THE INVENTION

Figure 1:
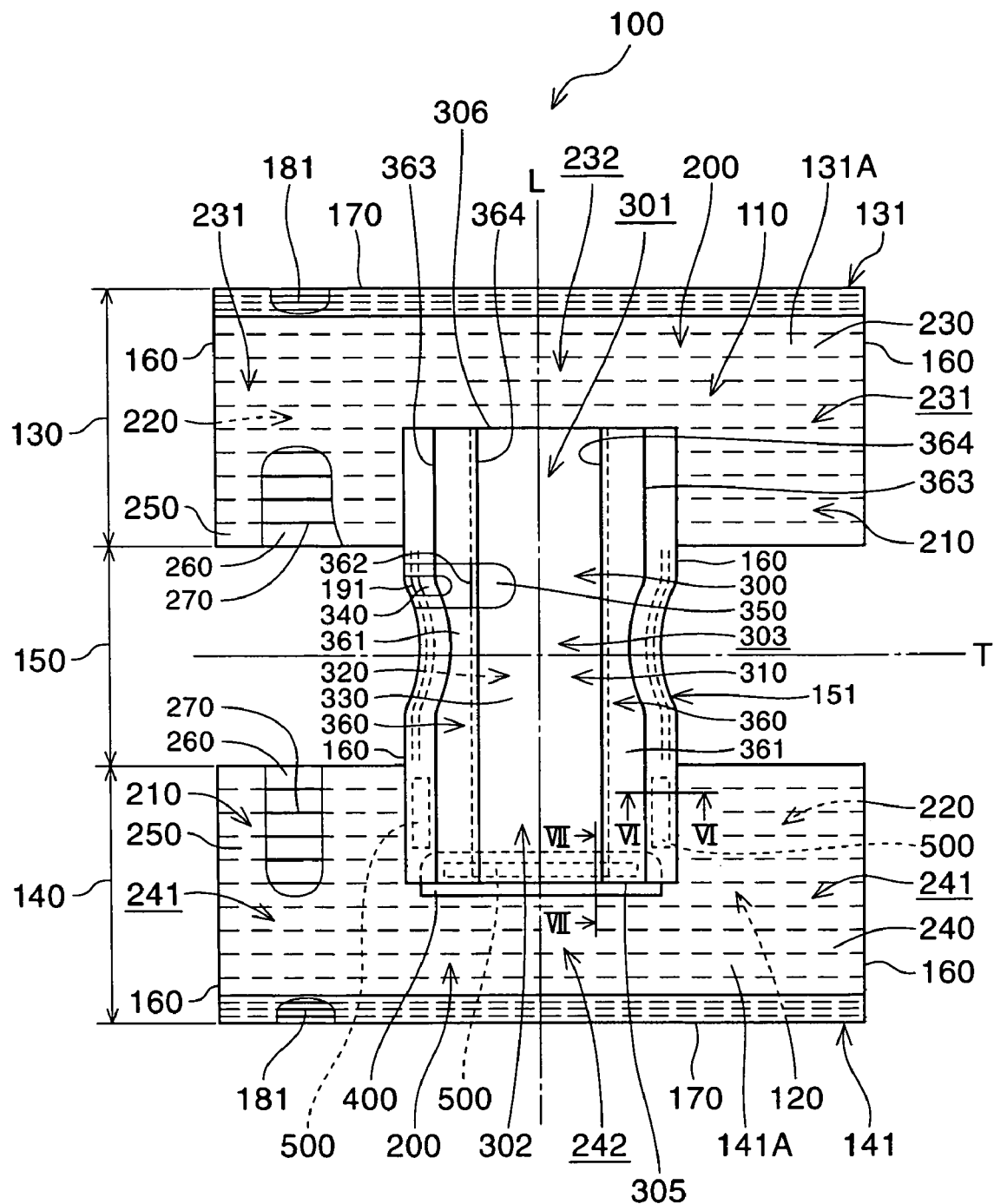
FIG. 1 is a top plan view of one embodiment of a garment of the present invention, and showing the wearer-facing surface of the garment.

The definitions of several terms are first provided to assist the reader in understanding the present invention.

The term "absorbent article(s)", as used herein, refers to devices which absorb and contain body exudates, and more specifically, refers to devices which are placed against or in proximity to the body of the wearer to absorb and contain the various exudates discharged from the body. Such devices include disposable diapers, training pants, supplemental inner pads used with disposable diapers, sanitary napkins, adult/infant incontinent garments used with or without supplemental inner pads, and the like. The term "comprising" and its derivatives, as used herein, are intended to be open ended terms that specify the presence of the stated features, elements, components, groups, integers, and/or steps, but do not exclude the presence of other, unstated features, elements, components, groups, integers, and/or steps. This definition also applies to words of similar meaning, for example, the terms "have", "include", "be provided with" and their derivatives. The term "disposable", as used herein, describes devices which generally are not intended to be laundered or otherwise restored or reused (i.e., they are intended to be discarded after a single use and, preferably, to be recycled, composted or otherwise disposed of in an environmentally compatible manner.) The terms "elastic" and "elastomeric" and their derivatives, as used herein, refer to a property of a material or a composite by virtue of which it tends to recover its original size and shape after removal of a force causing a deformation. The term "joined" or "joining", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e. one element is essentially part of the other element. This definition also applies to words of similar meaning, for example, the terms "attached", "bonded", "fixed" and their derivatives. The term "member" when used in the singular can have the dual meaning of a single element or a plurality of elements. The term "nonwoven", as used herein, refers to fabrics made of fibers held together by interlocking or bonding which are not woven, knitted, felted, or the like. The term "fabric", as used herein, may refer to a nonwoven web, a woven material, or other types of fabrics. The term "permanently attached", "permanently bonded", "permanently fixed" or "permanently joined", as used herein, refers to the joining, adhering, connecting, attaching, or the like, of two elements of an absorbent article such that the elements tend to be and remain bonded during normal use conditions of the garment. The term "pant-type garment", "pull-on type garment" and variations thereof, as used herein, refer to a garment (e.g., a disposable garment) having fixed edges and leg openings. A pant-type garment is placed in position on the wearer by inserting the wearer's legs into the leg openings and sliding the pant-type article into position about the wearer's lower torso. The term "refastenable", as used herein, refers to the property of two elements being capable of releasable attachment, separation, and subsequent releasable reattachment without substantial permanent deformation or rupture. The term "releasable", as used herein, refers to the property of two elements being capable of at least separation. The terms "releasably joinable", "releasably attachable", "releasably engageable", "releasably joined", "releasably attached", "releasably engaged" and variations thereof, as used herein, refer to two elements being connected or connectable such that the elements tend to remain connected in the absence of separation force applied to one or both of the elements, and the elements being capable of separation without substantial permanent deformation or rupture. The required separation force is typically beyond that encountered while wearing the absorbent article. The terms "releasably and repeatedly joined (joinable)" "releasably and repeatedly attached (attachable)", "releasably and repeatedly engaged (engageable)" and variations thereof, as used herein, refer to two elements capable of separation without substantial permanent deformation or rupture, and capable of being reconnected or reconnectable many times after such separation.

The garment 100 typically comprises a liquid pervious topsheet, a liquid impervious backsheet, and an absorbent core positioned between the topsheet and the backsheet in order to acquire and store bodily discharges. Alternatively, any of the topsheet, the backsheet and the absorbent core may be omitted from the components of the garment 100 if the garment 100 is a garment intended to be used with another absorbent article such as a supplemental inner pad.

FIGS. 1 to 10 illustrate one embodiment of a pant-type disposable garment of the present invention suitable for use as, but not limited to, an incontinence aid. FIG. 1 illustrates a top plan view of a pant-type disposable garment 100 according to the present invention, in its flat-out, uncontracted state (i.e., with elastic-induced contraction being pulled out) with portions of the structure being cut-away to show the underlying features. The present invention described herein is also applicable to a pant-type disposable garment such as a diaper cover or an incontinent garment used with a supplemental inner pad. As illustrated in FIG. 1, the garment 100 has a longitudinal centerline L. The term "longitudinal", as used herein, refers to a line, axis or direction in the plane of the garment 100 that is generally aligned with (e.g., approximately parallel to) a vertical plane which bisects a standing wearer into left and right body halves when the garment 100 is worn. The garment 100 illustrated in FIG. 1 also has a transverse centerline T. The terms "transverse" or "lateral", as used herein, are interchangeable, and refer to a line, axis or direction which lies within the plane of the garment 100 that is generally perpendicular to the longitudinal direction. The garment 100 has a periphery which is defined by side edges 160 and end edges 170. The garment 100 has two surfaces; one is a wearer-facing surface 110 and the other is an opposing surface 120. The wearer-facing surface 110 is the surface of the garment 100 which is generally oriented toward the wearer when the garment 100 is worn. The wearer-facing surface 110 typically at least partially comes in contact with the wearer's skin during use of the garment 100. The opposing surface 120 is the surface of the garment 100 which is generally oriented away from the wearer when the garment 100 is worn, and at least partially toward another garment if another garment is worn outside the garment 100. The garment 100 also has a first waist region 130, a second waist region 140 opposed to the first waist region 130, and a crotch region 150 positioned therebetween and connecting the first waist region 130 and the second waist region 140. The first waist region 130 and the second waist region 140 extend from the end edges 170 toward the crotch region 150. In one embodiment, the first and second waist regions 130, 140 may be the front and rear waist regions, respectively. Alternatively, the first and second waist regions 130, 140 may be the rear and front waist regions, respectively.

The garment 100 is configured to provide a pant configuration having a waist opening 180 and a pair of leg openings 190. The waist opening 180 is provided with one or more first elastic members 181 which at least partially, preferably entirely, form gathers along the circumference of the waist opening 180 for providing the fit of the garment 100 around the wearer's waist while the garment 100 is worn. Each leg opening 190 is provided with one or more second elastic members 191 which at least partially, preferably entirely, form gathers along the circumference of each leg opening 190 for providing the fit of the garment 100 around the wearer's leg while the garment 100 is worn.

The garment 100 comprises a first waist panel 131 positioned in the first waist region 130, a second waist panel 141 positioned in the second waist region 140 (the first and second waist panels may be collectively referred to as "waist panel"), and a crotch panel 151 positioned in the crotch region 150 and positioned between the first waist panel 131 and the second waist panel 141. In one embodiment, the first and second waist panels 131, 141 may be the front and rear waist panels, respectively. Alternatively, the first and second waist panels 131, 141 may be the rear and front waist panels, respectively. In the embodiment shown in FIGS. 1 to 5, the first waist panel 131 is the front waist panel and the second waist panel 141 is the rear waist panel. The crotch panel 151 is permanently joined to the first waist panel 131 by any known means such as adhesive, pressure bonding, heat bonding, etc., and is releasably joined to the second waist panel 141 by the releasable joint 500 which will be explained in detail hereinbelow. The crotch panel 151 is openable and reclosable with respect to the second waist panel 141. Alternatively, the crotch panel 151 may be releasably joined to both of the first waist panel 131 and the second waist panel 141 by releasable joints such that the crotch panel 151 may be openable and reclosable with respect to both of the first waist panel 131 and the second waist panel 141.

The garment 100 comprises a releasable joint 500 which releasably joins the crotch panel 151 to at least the second waist panel 141 to preform a pant shape of the garment 100. When it is necessary to first open the crotch panel 151 from the second waist panel 141, the releasable joint 500 is released. The term "releasable joint", as used herein, refers to a joint joining two elements to each other until intentional separation force is exerted on the joint while the joint is capable of being released without causing serious damage to the elements once intentional separation force is exerted on the joint. After the releasable joint 500 is first released, the releasable joint 500 may be incapable of joining the crotch panel 151 to the second waist panel 141. Alternatively, after the releasable joint 500 is first released, the releasable joint may be still capable of releasably joining the crotch panel 151 to the second waist panel 141. When the releasable joint 500 is released, the crotch panel 151 is openable from the second waist panel 141 such that the opening is provided for accessing the inside of the garment 100. Thus, the user can access the inside of the garment 100 to check the inside of the garment 100, to clean the inside of the garment 100, or to change the supplemental inner pad placed inside the garment 100 while the waist panel 131, 141 of the garment 100 is still anchored to the wearer. The crotch panel 151 must be reclosable with respect to the second waist panel 141 such that the garment 100 is reformed into a pant shape after the releasable joint 500 is released. For that purpose, the garment 100 further comprises a fastening member 400 being capable of refastening the crotch panel 151 to the second waist panel 141. When it is necessary to reopen the crotch panel to, e.g., check the inside of the garment 100, the user/caregiver separates the crotch panel 151 from the second waist panel 141 by releasing the fastening member 400. After the operation is done for the inside of the garment 100, the user/caregiver releasably reattaches the crotch panel 151 to the second waist panel 141 with the fastening member 400 to reform a pant shape of the garment 100.

Use of the releasable joint for preforming the pant shape of the garment is particularly useful in a pant-type disposable garment which has an openable crotch panel. If the openable crotch panel is joined to the second waist panel by the fastening member to preform the pant shape, the fastening member may unfasten or may be damaged due to the force exerted to the fastening member while pulling up the garment on the wearer. In order to prevent the issue of unfastening or damage of the fastening member, it would be possible to enhance the anchoring force of the fastening member for joining the crotch panel to the second waist panel. In such a case, however, the user would experience difficulty in separating and opening the crotch panel from the second panel because of the high anchoring force of the fastening member. In the pant-type disposable garment of the present invention, the releasable joint preforms a pant shape of the garment and the releasable joint undergoes the pulling force to pull up the garment. Therefore, the fastening member may not be fastened to preform the pant shape of the garment and is protected from the pulling force. Alternatively, even if the fastening member is fastened to join the crotch panel to the second waist panel before use of the garment, the force exerted to the fastening member is tempered such that the fastening member is protected from the pulling force because of the presence of the releasable joint to preform the pant shape.

Figure 2:
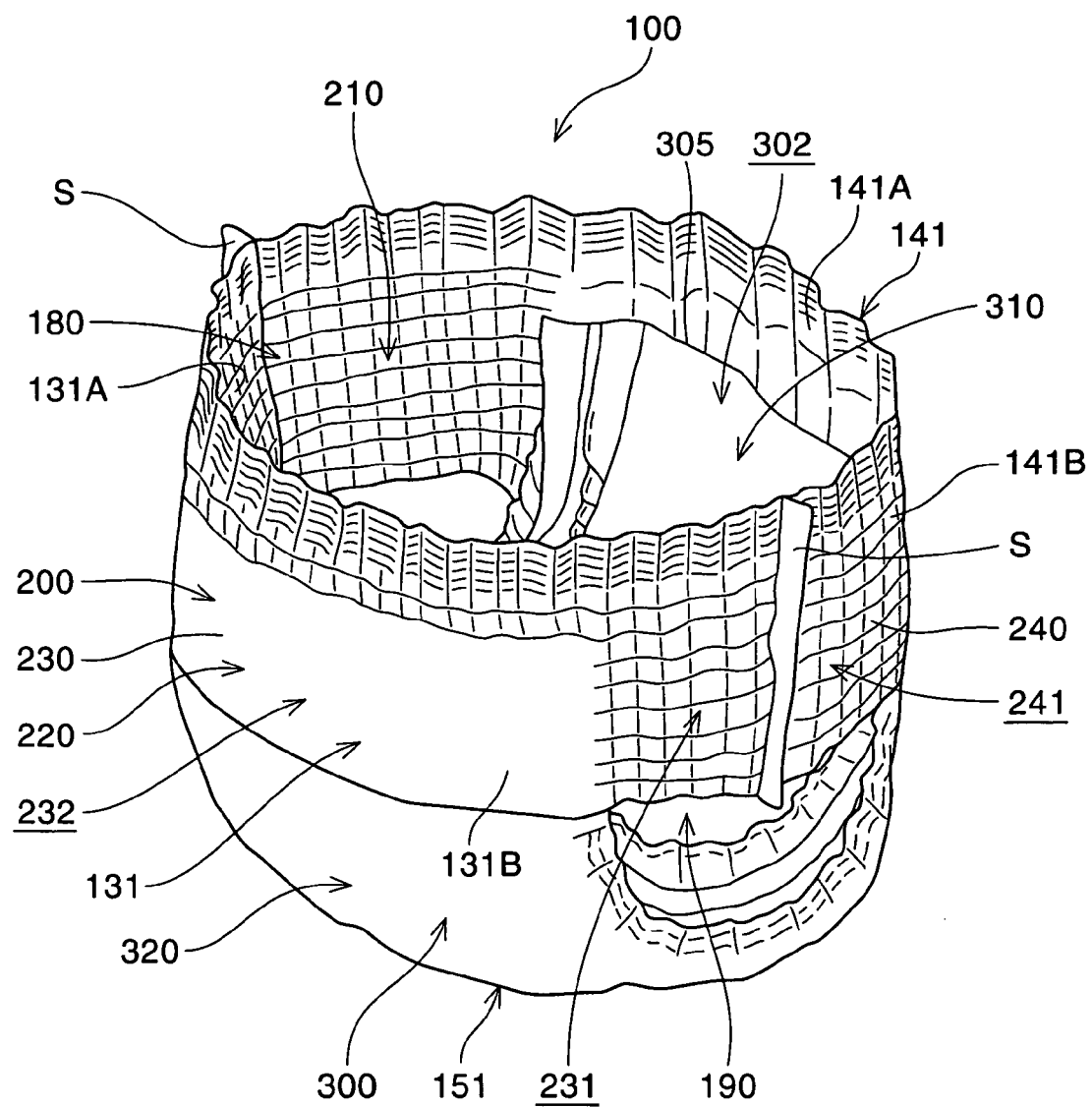
FIG. 2 is a schematic perspective view of the garment illustrated in FIG. 1 before the releasable joint is released, and showing the first waist region of the garment.

The waist panel 131, 141 encircles the waist of the wearer, and makes the crotch panel fit to the wearer's body while the garment 100 is worn. As illustrated in FIGS. 1 and 2, the waist panel 131, 141 has typically two surfaces; one is an interior surface 131A, 141A and the other is an exterior surface 131B, 141B. The interior surface 131A, 141A is the surface of the waist panel 131, 141 which is generally oriented toward the wearer when the garment 100 is worn. The interior surface 131A, 141A typically at least partially comes in contact with the wearer's skin during use of the garment 100. The exterior surface 131B, 141B is the surface of the waist panel 131, 141 which is generally oriented away from the wearer when the garment 100 is worn, and at least partially toward another garment if another garment is worn.

The waist panel 131, 141 can be made from a unitary piece of material or from a number of separate pieces of material that may be identical or different. In the embodiment illustrated in FIGS. 1 to 5, the first waist panel 131 comprises two first side segments 231 adjacent to one of the side edges 160 and a first central segment 232 positioned between the first side segments 231. The first central segment 232 typically covers the ventral waist of the wearer when the garment 100 is worn. The second waist panel 141 comprises two second side segments 241 adjacent to one of the side edges 160 and a second central segment 242 positioned between the second side segments 241. The second central segment 242 typically covers the dorsal waist of the wearer when the garment 100 is worn. As illustrated in FIGS. 2 to 5, each first side segment 231 is permanently joined to each second side segment 241 at the side seams S to form a ring-like waist panel 200. Heat bonds, pressure bonds, ultrasonic bonds, or any other suitable means or combinations thereof as are known in the art can be used for bonding the first side segment 231 and the second side segment 241 to each other.

The waist panel 131, 141 may comprise one or multiple layers, preferably two or three layers. As illustrated in FIG. 1, the waist panel 131, 141 comprises two layers, which comprises an interior layer 250 and an exterior layer 260. The interior layer 250 is positioned on the interior surface 131A, 141A, and typically at least partially contacts with the wearer's skin when the garment 100 is worn. The exterior layer 260 is positioned on the exterior surface 131B, 141B of the waist panel 131, 141, and typically at least partially contacts with the garments of the wearer if another garment is worn. The waist panel 131, 141 can be elasticized by one or more elastic strands 270 disposed between the interior layer 250 and the exterior layer 260 for providing the fit of the waist panel 131, 141 around the wearer's torso while the garment 100 is worn. The elastic strands 270 allow the waist panel 131, 141 to elastically expand and contract such that the waist panel 131, 141 dynamically fits the wearer's body during use.

The waist panel 131, 141 preferably comprises a nonwoven material. Such a nonwoven material for the waist panel 131, 141 is preferably air pervious. However, embodiments are contemplated wherein the waist panel 131, 141 comprises materials such as woven webs, scrims, films, loose fibers, or any other material or combination of materials known in the art that will give the waist panel 131, 141 a cloth-like look and/or feel and is at a minimum air permeable. If the waist panel 131, 141 comprises two layers, i.e., the interior layer 250 and the exterior layer 260, such layers may in particular comprise any material such as a nonwoven or a polymeric film. In a preferred embodiment, the layers may be formed from a laminate comprising two nonwoven layers, or a nonwoven layer and a polymeric film. The layer positioned on the interior surface 131A, 141A of the waist panel 131, 141 is preferably provided with a nonwoven layer. Such a nonwoven layer presents a compliant surface to the skin of a wearer and thus greatly improves skin healthiness. The waist panel 131, 141 may also comprise three layers; one film layer and two nonwoven layers. Preferably, the film may be interposed between the two nonwoven layers. This sequence of layers results in a closed fibrous structure, which has a particularly pleasing sensation on contact with the skin of a wearer.

Suitable nonwoven layers for the waist panel 131, 141 may comprise felt fabrics, spunlaced fabrics, fluid jet entangled fabrics, air-laid fabrics, wet-laid fabrics, dry-laid fabrics, melt-blown fabrics, staple fiber carding fabrics, spunbonded fabrics, stitch-bonded fabrics, apertured fabrics, combinations of the above or the like. The nonwoven layer or the nonwoven layers constituting the waist panel 131, 141 may be hydrophobic or hydrophilic. Suitable film materials for the waist panel 131, 141 may comprise a thermoplastic material. The thermoplastic material can be selected from among all types of polyolefins especially polyethylene, polypropylene, amorphous polyolefins, and the like; material containing meltable components comprising fibers or polymeric binders including natural fibers such as cellulose, wood pulp, cotton, jute, hemp; synthetic fibers such as fiberglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those supplied by EXXON Chemical Co., III, US under the designation EXXAIRE or those supplied by Mitsui Chemical Co., Japan under the designation ESPOIR NO; and monolithic breathable materials such as Hytrel™ available from DuPont and Pebax™ available from ELF Atochem, France.

The crotch panel 151 has two surfaces; one is an inner surface 310 and the other is an outer surface 320 as illustrated in FIG. 1. The inner surface 310 is the surface of the crotch panel 151 which is generally oriented toward the wearer when the garment 100 is worn. The inner surface 310 typically at least partially comes in contact with the wearer's skin during use of the garment 100. The outer surface 320 is the surface of the crotch panel 151 which is generally oriented away from the wearer when the garment 100 is worn, and at least partially toward another garment if another garment is worn. The crotch panel may be an assembly typically comprising a liquid pervious topsheet, a liquid impervious backsheet, and an absorbent core in order to acquire and store bodily discharges. The crotch panel may further comprise other features added to form the composite absorbent assembly structure. Alternatively, the crotch panel may only comprise a liquid impervious sheet to, e.g., hold a supplemental inner pad inside.

In the embodiment shown in FIG. 1, the first waist panel 131, the second waist panel 141 and the crotch panel 151 comprise separate members from each other. The crotch panel 151 has a first portion 301 including a fixed end 306 permanently joined to the first waist panel 131 and a second portion 302 including an openable end 305 openable with respect to the second waist panel 141. The first portion 301 overlaps with the first central segment 232 and the second portion 302 overlaps with the second central 242. The fixed end 306 is permanently joined to the interior surface 131A of the first waist panel 131. Preferably, the first portion overlapping with the first central segment 302 is permanently joined to the interior surface 131A of the first waist panel 131. The openable end 305 is releasably joined to the interior surface 141A of the second waist panel 141 by the releasable joint 500. After the releasable joint 500 is released, the openable end 305 is reclosable to the exterior surface 141B of the second waist panel 141 by the fastening member 400 being capable of refastening the openable end 305 of the crotch panel 151 to the second waist panel 141. In an alternative embodiment, the crotch panel 151 may have opposed openable ends; one openable end being openable with respect to the second waist panel 141 and the other openable end being openable with respect to the first waist panel 131. The releasable joint may be provided adjacent to the opposite openable ends of the crotch panel and the fastening member may be provided adjacent to the opposite openable ends such that both of the opposite openable ends are openable and reclosable to both of the first and second waist panels.

Figure 14:
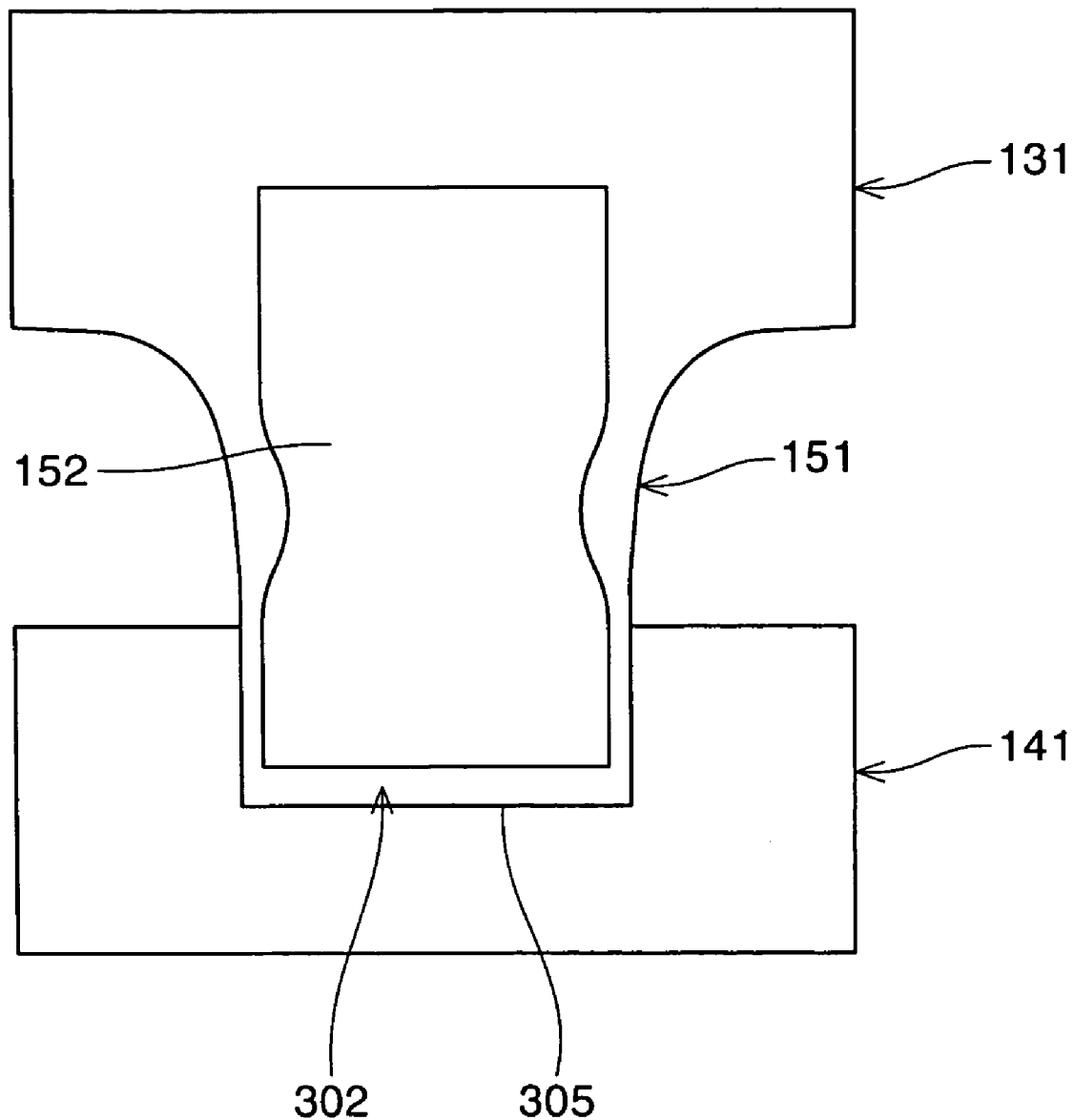
FIG. 14 is a schematic top plane view of alternative embodiment of the garment of the present invention.

FIG. 14 shows a schematic view of an alternative embodiment of panel structures of the pant-type disposable garment. The garment 100 has a first waist panel 131, the second waist panel 141 and a crotch panel 151. The crotch panel 151 comprises an integral material of the first waist panel 131 instead of the separate crotch panel being permanently joined to the first waist panel 131. The crotch panel 151 has an openable portion 302 including an openable end 305 being openable and reclosable with respect to the second waist panel 141. In the embodiment shown in FIG. 14, an absorbent assembly 152 comprising a topsheet, a backsheet and an absorbent core may be disposed at least in the crotch panel 151.

Figure 6:
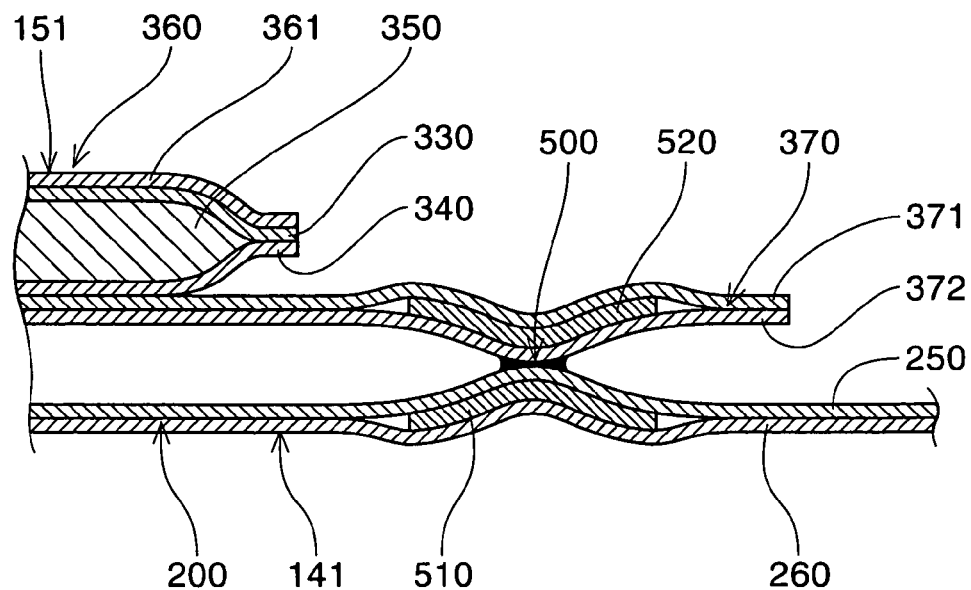
FIG. 6 is a cross-sectional view taken along line VI-VI of FIG. 1.
Figure 7:
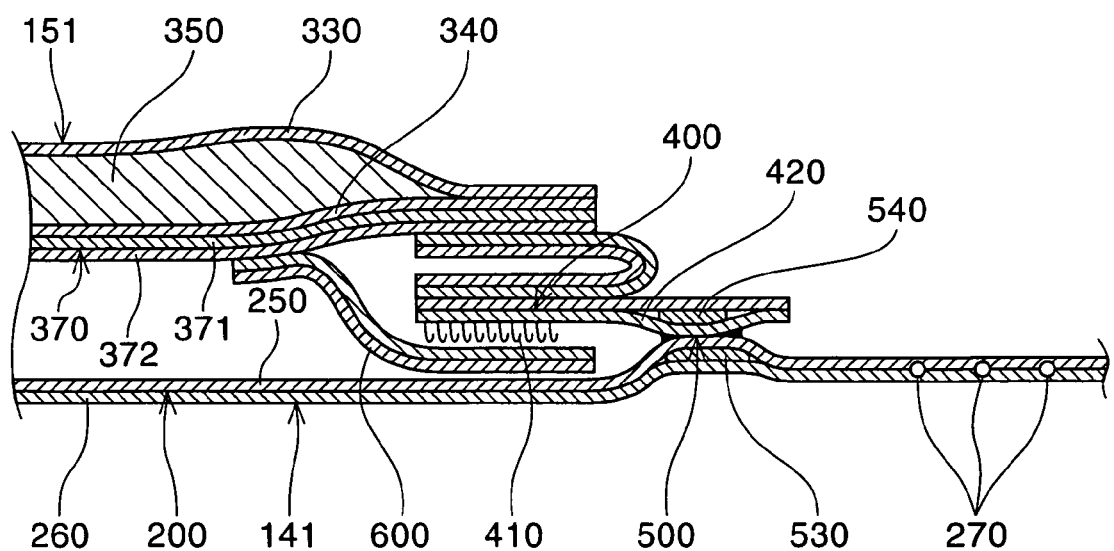
FIG. 7 is a cross-sectional view taken along line VII-VII of FIG. 1.
Figure 8:
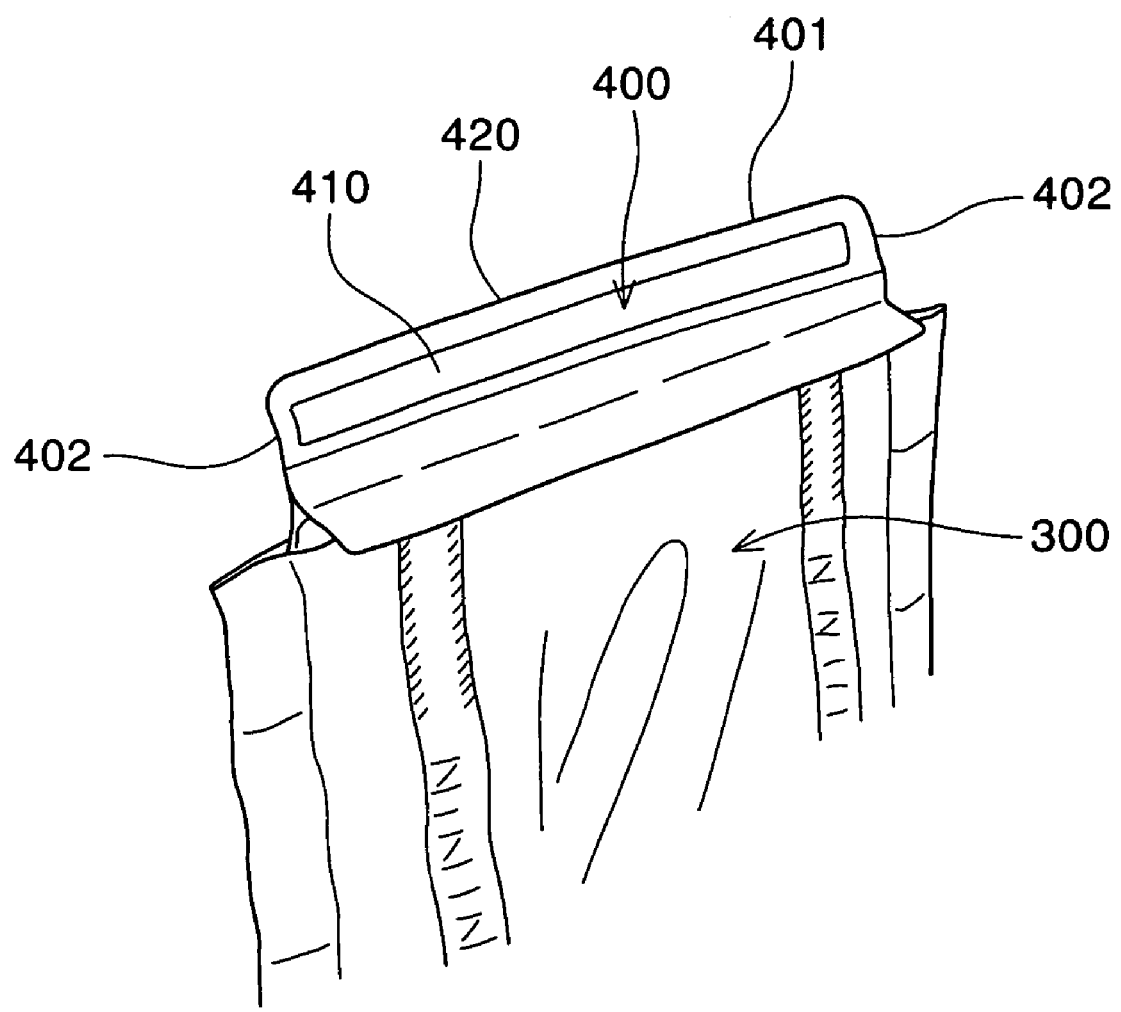
FIG. 8 is a schematic perspective view of one embodiment of the fastening member when the fastening member is permanently fixed to the crotch panel.

The crotch panel 151 comprises a liquid pervious topsheet 330, a liquid impervious backsheet 340, an absorbent core 350 positioned between the topsheet 330 and the backsheet 340. The crotch panel 151 preferably further comprises a pair of elasticized barrier cuffs 360. The topsheet 330 is preferably positioned so as to be adjacent to the inner surface of the absorbent core 350 and is preferably joined thereto and to the backsheet 340 in any suitable manner as is well known in the art. Such manners are described below with respect to joining the backsheet 340 to the absorbent core 350. The topsheet 330 and the backsheet 340 may be joined directly to each other. Alternatively, the topsheet 330 and the backsheet 340 may be indirectly joined together by directly joining them to other elements such as the absorbent core 350, the elasticized barrier cuffs 360 and the like in any suitable manner as is well known in the art. The backsheet 340 is preferably positioned so as to be adjacent to the outer surface of the absorbent core 350 and is preferably joined thereto in any suitable manner as is well known in the art. For example, the backsheet 340 may be secured to the absorbent core 350 by a uniform continuous layer of adhesive, a patterned layer of adhesive, or an array of separate lines, spirals, or spots of adhesive. Adhesives which have been found to be satisfactory are manufactured by H.B. Fuller Company of St. Paul, Minn. and marketed as HL-1258. Heat bonds, pressure bonds, ultrasonic bonds, dynamic mechanical bonds, or any other suitable means or combinations thereof as are known in the art may be used. While the topsheet 330, the backsheet 340, and the absorbent core 350 may be assembled in a variety of well known configurations in order to form a crotch panel 151, exemplary assembly configurations are described generally in U.S. Pat. No. 5,074,854 and International Patent Publication No. WO 90/04375. Further, as illustrated in FIGS. 6 and 7, the crotch panel 151 may further comprise an outermost layer 370 of nonwoven laminated on the outer surface of the backsheet 340 to provide the garment 100 with more cloth-like appearance in the crotch region 150 if the outer surface 320 of the crotch panel 151 is exposed. The outermost layer 370 typically comprises an inner nonwoven layer 371 and an outer nonwoven layer 372. In such an embodiment, any of the topsheet 330, the backsheet 340 and the absorbent core 350 may be omitted from the components of the crotch panel 151 if the garment 100 is intended to be used with another absorbent article such as a supplemental inner pad.

The topsheet 330 is adapted to contact the wearer's skin. The topsheet 330 faces the wearer while the garment 100 is worn, and is suitably employed to help isolate the wearer's skin from bodily discharges held in the absorbent core 350. Thus, the topsheet 330 is preferably compliant, soft feeling, and non-irritating to the wearer's skin. Further, the topsheet 330 may be less hydrophilic than the absorbent core 350 to present a relatively dry surface to the wearer. The topsheet 330 may also be liquid pervious for permitting liquid discharges (e.g., urine) to readily penetrate through its thickness. A suitable topsheet may be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be composed of natural fibers (e.g., wood or cotton fibers), synthetic fibers (e.g., polymeric fibers such as polyester, polypropylene, polyolefin, or polyethylene fibers), or a combination of natural and synthetic fibers. For example, the topsheet 330 may be composed of a meltblown or spunbonded web of polyolefin fibers. The topsheet 330 may also be a bonded-carded web composed of natural and/or synthetic fibers. Further, the topsheet 330 may be composed of a substantially hydrophobic material, and the hydrophobic material may optionally be treated with a surfactant or otherwise processed to impart a desired level of wettability and hydrophilicity. Such surfactants may be applied by any conventional means, such as spraying, printing, brush coating or the like. Surfactants may be applied to the entire topsheet 330 or may be selectively applied to particular sections of the topsheet 330, such as the medial section along the longitudinal centerline of the garment, to provide greater wettability of such sections. The topsheet 330 may further include a composition applied thereto that is configured to be transferred to the wearer's skin for improving the skin health of the wearer.

The backsheet 340 is to prevent bodily discharges absorbed and contained in the absorbent core 350 from wetting other articles which contact the garment 100 such as bed sheets and undergarments. Thus, the backsheet 340 is preferably impervious to liquids (e.g., urine), and is preferably manufactured from a thin plastic film although other flexible liquid impervious materials may also be used. As used herein, the term "flexible" refers to materials which are compliant and will readily conform to the general shape and contours of the human body. A suitable material for the backsheet 340 is a thermoplastic film having a thickness of from about 0.012 mm (0.5 mil) to about 0.051 mm (2.0 mils), preferably comprising polyethylene or polypropylene. If it is desired to present the backsheet 340 with a more cloth-like feel, the backsheet 340 may comprise a polyolefin film having a nonwoven web laminated to the exterior surface thereof, such as a spunbond web of polyolefin fibers. Further, the backsheet 340 may be formed of a woven or nonwoven fibrous web layer that has been totally or partially constructed or treated to impart a desired level of liquid impermeability to selected regions that are adjacent or proximate to the absorbent core 350. Still further, the backsheet 340 may be optionally composed of a microporous "breathable" material that permits vapors to escape from the garment 100 while still preventing liquid discharges form passing through the backsheet 340. For example, the backsheet 340 may include a vapor permeable nonwoven facing layer laminated to a micro-porous film. The backsheet 340 may also be an elastomeric material, such as a stretch-thermal laminate ("STL"), neck-bonded laminate ("NBL"), or stretch-bonded laminate ("SBL") material. The backsheet 340 can also be embossed or otherwise provided with a matte finish to provide a more aesthetically pleasing appearance.

The absorbent core 350 may be any absorbent member which is generally compressible, conformable, non-irritating to the wearer's skin, and capable of absorbing and retaining liquids such as urine and other certain body discharges. The absorbent core 350 may be manufactured in a wide variety of sizes and shapes (e.g., rectangular, hourglass, "T"-shaped, asymmetric, etc.) and from a wide variety of liquid-absorbent materials commonly used in disposable diapers and the other absorbent articles such as comminuted wood pulp which is generally referred to as airfelt. Examples of other suitable absorbent materials include creped cellulose wadding; meltblown polymers including coform; chemically stiffened, modified or cross-linked cellulose fibers; tissue including tissue wraps and tissue laminates; absorbent foams; absorbent sponges; superabsorbent polymers; absorbent gelling materials; or any equivalent material or combinations of materials. Preferably, the absorbent core 350 includes superabsorbent particles and a carrier means for the superabsorbent particles. Such superabsorbent particles are typically manufactured from an absorbent gelling material. Preferably, the carrier means may be formed from comminuted wood pulp. Such comminuted wood pulp may be exchanged with synthetic, polymeric, meltblown fibers or with a combination of meltblown fibers and natural fibers. The configuration and construction of the absorbent core 350 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 350 may also be varied to accommodate wearers ranging from infants through adults. However, the total absorbent capacity of the absorbent core 350 should be compatible with the intended use of the garment 100. The absorbent core 350 may further comprise an acquisition/distribution layer of chemically stiffened fibers and a fluid storage layer positioned underneath the acquisition/distribution layer.

The crotch panel 151 preferably further comprises a pair of elasticized barrier cuffs 360 for providing improved containment of liquids and other bodily discharges. The elasticized barrier cuff 360 typically comprises a barrier sheet 361 and an elastic spacing member 362. The elasticized barrier cuff 360 has a fixed edge 363 and a free edge 364. The fixed edge 363 is joined to the underlying component, such as the topsheet 330, the backsheet 340, the absorbent core 350, and the like, in any suitable manner as is well known in the art. The elastic spacing member 362 is enclosed by the barrier sheet 361 such that the elastic spacing member 362 is adjacent to the free edge 364 of the elastic barrier cuff 360. The elastic spacing member 362 allows the free edge 364 of the barrier cuff 360 to stand up away from the topsheet 330 in the crotch region 150 of the garment 100. While such an elasticized barrier cuff may comprise several different embodiments for reducing the leakage of bodily discharges, exemplary structures are described generally in U.S. Pat. No. 4,695,278; U.S. Pat. No. 4,795,454; and U.S. Pat. No. 5,685,874. The elasticized barrier cuffs 360 may be manufactured from a wide variety of materials such as polypropylene, polyester, rayon, nylon, foams, plastic films, formed films, and elastic foams. The barrier cuffs 360 may be woven, non-woven, spun-bonded, carded, or the like. A preferred barrier cuff comprises a polypropylene material containing no additional finish or surfactant to render it liquid impermeable.

As explained hereinabove, the leg opening 190 is provided with the elastic members 191. The elastic member 191 may be disposed along a portion of the side edge of the crotch panel 151 as shown in FIG. 1. However, the elastic member 191 may be disposed along the entire length of the side edge of the crotch panel 151.

The releasable joint 500 releasably joins the crotch panel 151 to the second waist panel 141 to preform the pant shape of the garment 100. The releasable joint 500 is capable of being released to open the crotch panel 151 by intentional separation force exerted on the releasable joint 500 without causing serious damage to components of the garment 100. The releasable joint 500 may be provided to join a portion of the second waist panel 141 and a portion of the crotch panel 151 as shown in the embodiment shown in FIGS. 6 and 7, more concretely to join the interior layer 250 of the second waist panel 141 and the outermost layer 370 of the crotch panel 151. In the embodiment shown in FIGS. 1 and 3, the releasable joint 500 may comprise three components; one component extending in the lateral direction along and adjacent the openable end 305 of the crotch panel and the other two components extending in the longitudinal direction along and adjacent the side edge of the crotch panel 151. Alternatively, the releasable joint 500 may be formed with two or more of discrete components such as dots which extend intermittently in the lateral direction of the garment 100.

The releasable joint 500 may be formed any known means such as heat bonds, pressure bonds, ultrasonic bonds, cohesive bonds, adhesive bonds, perforations, or any other suitable means or combinations thereof. In the embodiment, the releasable joint 500 is provided between and joins the second waist panel 141 and the outermost layer 370 of the crotch panel 151. The second waist panel 141 is provided with an elastomeric layer 510 sandwiched the interior and exterior layers 250, 260, and the outermost layer 370 is provided with an elastomeric layer 520 sandwiched between the inner and outer nonwoven layers 371, 372. In the embodiment shown in FIG. 7, the releasable joint 500 is provided between and joins the second waist panel 141 and the substrate 420 of the fastening member 400 instead of the outermost layer 370 of the crotch panel 151. The second waist panel 141 is provided with an elastomeric layer 530 sandwiched between the interior and exterior layers 250, 260, and the substrate 420 comprises two nonwoven layers and an elastomeric layer 540 sandwiched between the nonwoven layers.

The releasable joint 500 is preferably formed to resist separation force that occurs during use and/or application of the garment 100. The term "separation force", as used herein, refers to forces to separate one component of the garment 100 from another component of the garment 100 when such components are attached to each other. Separation force typically includes shear force and peel force. The term "shear force", as used herein, refers to separation force acting generally parallel to the plane where the releasable joint 500 is formed. The term "peel force", as used herein, separation force acting in the direction away from the wearer when the garment 100 is worn. The shear force to release the releasable joint 500 should not be too small since the components joined to each other by the releasable joint 500 undesirably separated from each other during use of the garment 100. It can results in serious leakage of bodily discharges which may cause soil of the wearer's clothes. In contrast, the peel force to release the releasable joint 500 should not be too great since it is difficult for users and/or caregivers to release the releasable joint 500 in order to use the garment 100 as a pant-type refastenable diaper. In such a case, if the user/caregiver forcibly tries to release the releasable joint 500, the components of the garment 100 may tear when the releasable joint 500 is released. The elastomeric layers 510, 520, 530 and 540 sandwiched between nonwoven layers allow the shear force and the peel force of the releasable joint 500 to be optimized. Suitable materials for the elastomeric layer can include synthetic rubber, natural rubber, thermoplastic olefinic elastomer, thermoplastic polyurethane elastomer, thermoplastic polyamide elastomer or the like. The shear force to release the releasable joint 500 is preferably greater than about 3.9 N/cm, more preferably ranges between about 5.9 N/cm and about 23.6 N/cm. The peel force to release the releasable joint 500 is preferably smaller than about 3.9 N/cm, more preferably ranges between about 0.079 N/cm and about 2.0 N/cm.

The following method describes the procedure for measuring the peel force and the shear force, in N/cm, to release the releasable joint 500. A suitable instrument used for the measurement of the peel force and the sear force to release the releasable joint 500 is INSTRON 5564 which may be equipped with either digital readout or strip chart data display for load and elongation. The following procedure is conducted under standard laboratory conditions at 23° C. (73° F.) and 50% relative humidity.

(1) Take a fresh garment from a package and cut a sample strip from the garment centered about the releasable joint. The sample strip comprises portions of the crotch panel and the waist panel having 25.4 mm (in the transverse direction) by 100 mm (in the longitudinal direction) size for each, and the portions should be releasably jointing each other. At least three (3) sample strips should be prepared for each measurement of the shear force and the peel force.

(2) Put the sample strip in the instrument. The way to set the sample strip is to insert one end of the portion taken from the crotch panel into the top clamp of the instrument first, and then to insert another end of the portion taken from the waist panel into the bottom clamp with enough tension to eliminate any slack of the sample strip.

(3) Pull the sample strip at a pulling speed of 500 mm/minute until completely separating the portion of crotch panel and the waist panel each other. This procedure is based on the International Standard ISO 527, which is incorporated herein by reference.

(4) Read the peak value of the shear or peel force value during the procedure (3).

(5) Repeat the above procedures (1) to (4) for the other sample strips.

(6) Calculate the Shear Force or the Peel Force as follows:

$$\text{Shear/Peel Force (N/cm)} = \frac{\text{Sum of the peak force values of the procedure (4) for samples tested}}{\text{Number of test strips tested}}$$

The fastening member 400 is provided on and permanently fixed to the crotch panel 151 adjacent to the openable end 305. The fastening member 400 is capable of refastening the crotch panel 151 to the second waist panel 141 to reform the pant shape of the garment 100 after the releasable joint 500 is released. In a preferred embodiment, the fastening member 400 is capable of refastening the openable end 305 of the crotch panel 151 with the exterior surface 141B of the second waist panel 141. Alternatively, the fastening member 400 may be capable of refastening the crotch panel 151 with the interior surface 141A of the second waist panel 141.

In a preferred embodiment, the fastening member 400 comprises one or more patches of hook-type material which is complementary to the second waist panel 141. In that case, the second waist panel 141 typically comprises receiving material complementary to the hook-type material of the fastening member 400. Alternatively, the fastening member 400 may comprise one or more patches of receiving material if the second waist panel 141 comprises hook-type material complementary to the receiving material of the fastening member 400. The term "hook-type material", as used herein, refers to any material having a fastening system joined to and projecting from a substrate. The fastening system may have one or more mechanical engaging means which project, typically radially, from a shank which is joined to the substrate. The engaging means is typically the portion of the hook-type material which penetrates and is secured to the exposed surface of the complementary receiving material. Suitable hook-type material is sold by the Minnesota Mining and Manufacturing Company of Minneapolis, Minn. as Model Number XPO-0040 and by Velcro U.S.A., Inc. of Manchester, N.H. as Hook 88. The term "receiving material", as used herein, refers to any material having an exposed surface with tightly spaced openings complementary to the hook-type material. Such openings are typically defined by one or more strands or fibers. The complementary hook-type material may be entrapped by the exposed surface of the receiving material, and may not be withdrawn without interference. Suitable materials for such receiving material can include loop material, nonwoven material or the like. Such receiving material may also comprise Model Number CX-780 sold by KURARAY Corp. For the embodiment described herein, loop material having a pile depth of about 0.8 millimeters works well as a receiving material. Hook-type material and receiving material are considered "complementary" if the openings between the strands or fibers are sized to allow at least one engaging means of the hook-type material to penetrate into the exposed surface of the receiving material and to be engaged or intercepted thereby.

As illustrated in FIGS. 4, and 7 to 10, the fastening member 400 comprises a patch 410 of hook-type material which is complementary to the exterior surface 141B of the second waist panel 141, and a substrate 420 to which the patch 410 is attached. The patch 410 may be integral with the substrate 420, or may be a separate element attached to the substrate 420. The patch 410 may be spaced inwardly from the transverse side edges 401 and the longitudinal end edge 402 of the fastening member 400 at least approximately 0.1 centimeters, to provide for variations in positioning during manufacture, and to prevent the rough edge of the patch 410 from contacting and irritating the skin of the wearer. The patch 410 may be provided in any shape as long as the fastening member 400 is capable of refastening the crotch panel 151 to the second waist panel 141. Such suitable shapes include, but are not limited to: circle or oval shape; semicircle shape; sector shape; triangle shape; square, rectangular or diamond shape; a polygonal shape such as pentagon, hexagon, or the like; or any combination of the above. The patch 410 may be permanently bonded to the substrate 420 by any means well known in the art such that the joining strength exceeds the desired peel and shear strength. In another embodiment (not shown), the fastening member 400 may comprise one or more patches of adhesive instead of patches of hook or loop-type material. Suitable adhesive is sold by Eastman Chemical Products Company of Kingsport, Tenn. under the tradename Eastobond A-3. If adhesive patches are selected for the fastening member 400, the second waist panel 141 should be adapted to provide a complementary attachment surface to which such adhesive patches will readily adhere. A polyethylene material is suitable for providing the second waist panel 141 with such a complementary attachment surface.

Figure 3:
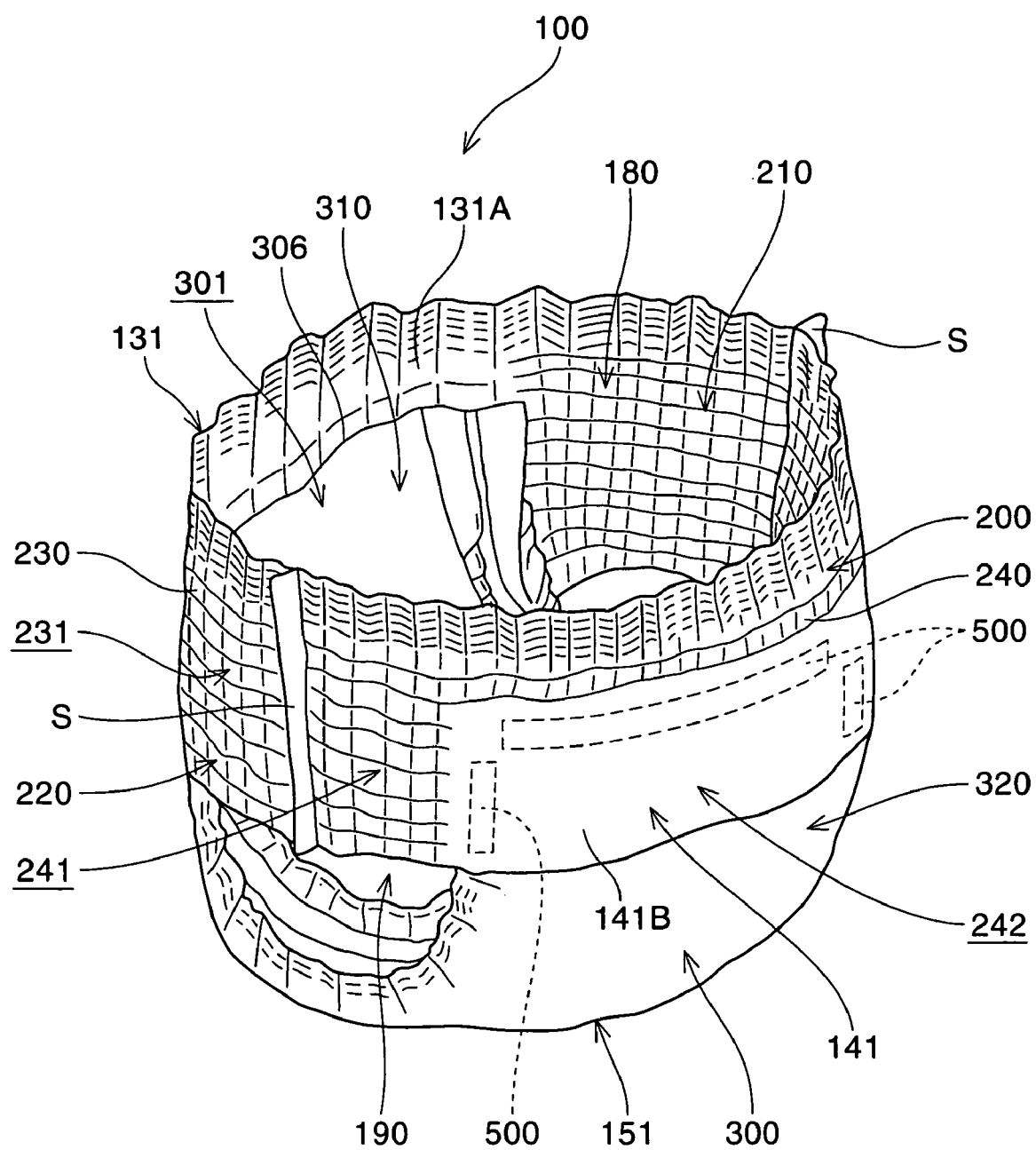
FIG. 3 is a schematic perspective view of the garment illustrated in FIG. 1 before the releasable joint is released, and showing the second waist region of the garment.
Figure 4:
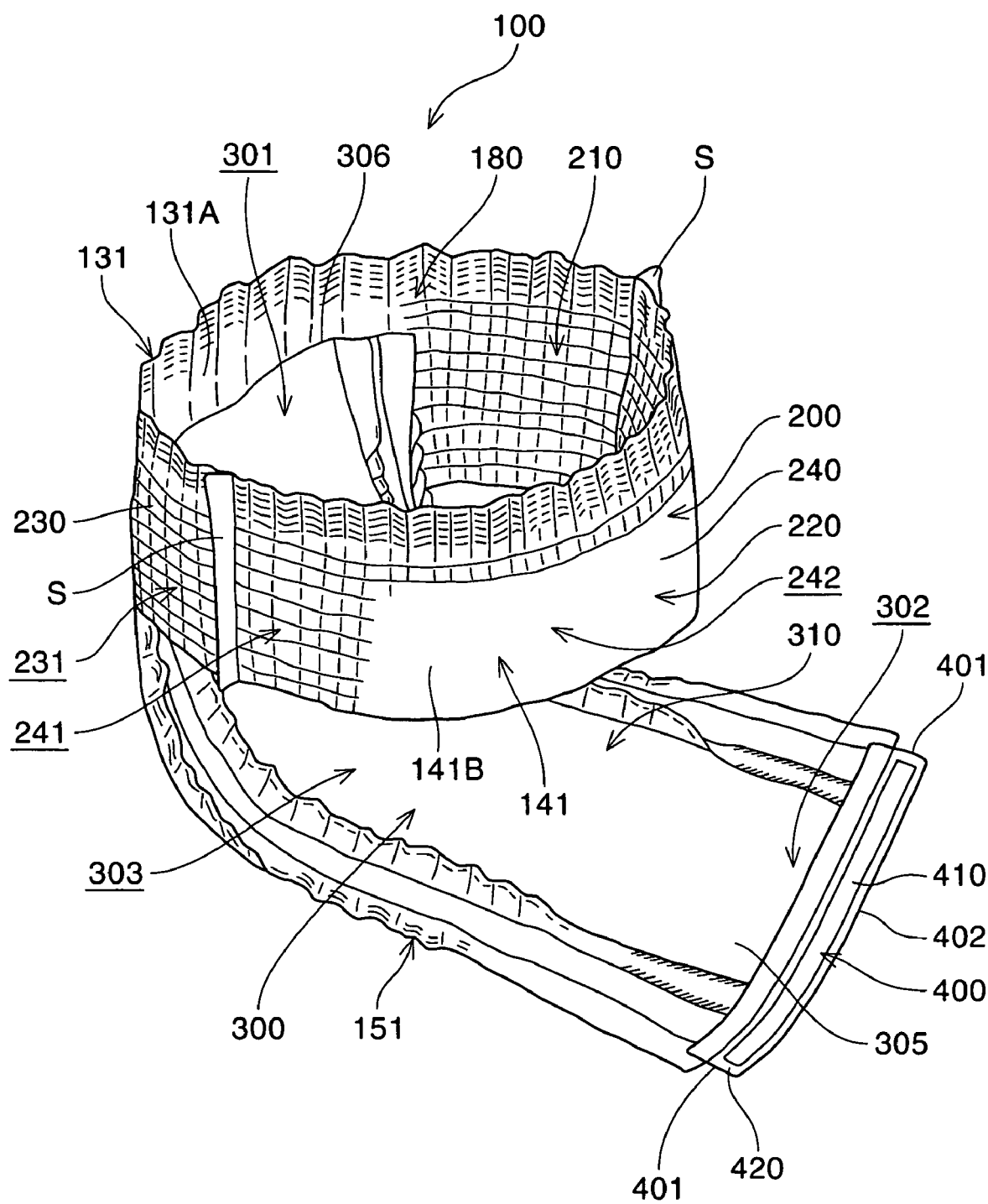
FIG. 4 is a schematic perspective view of the garment illustrated in FIG. 1 after the releasable joint is released.
Figure 5:
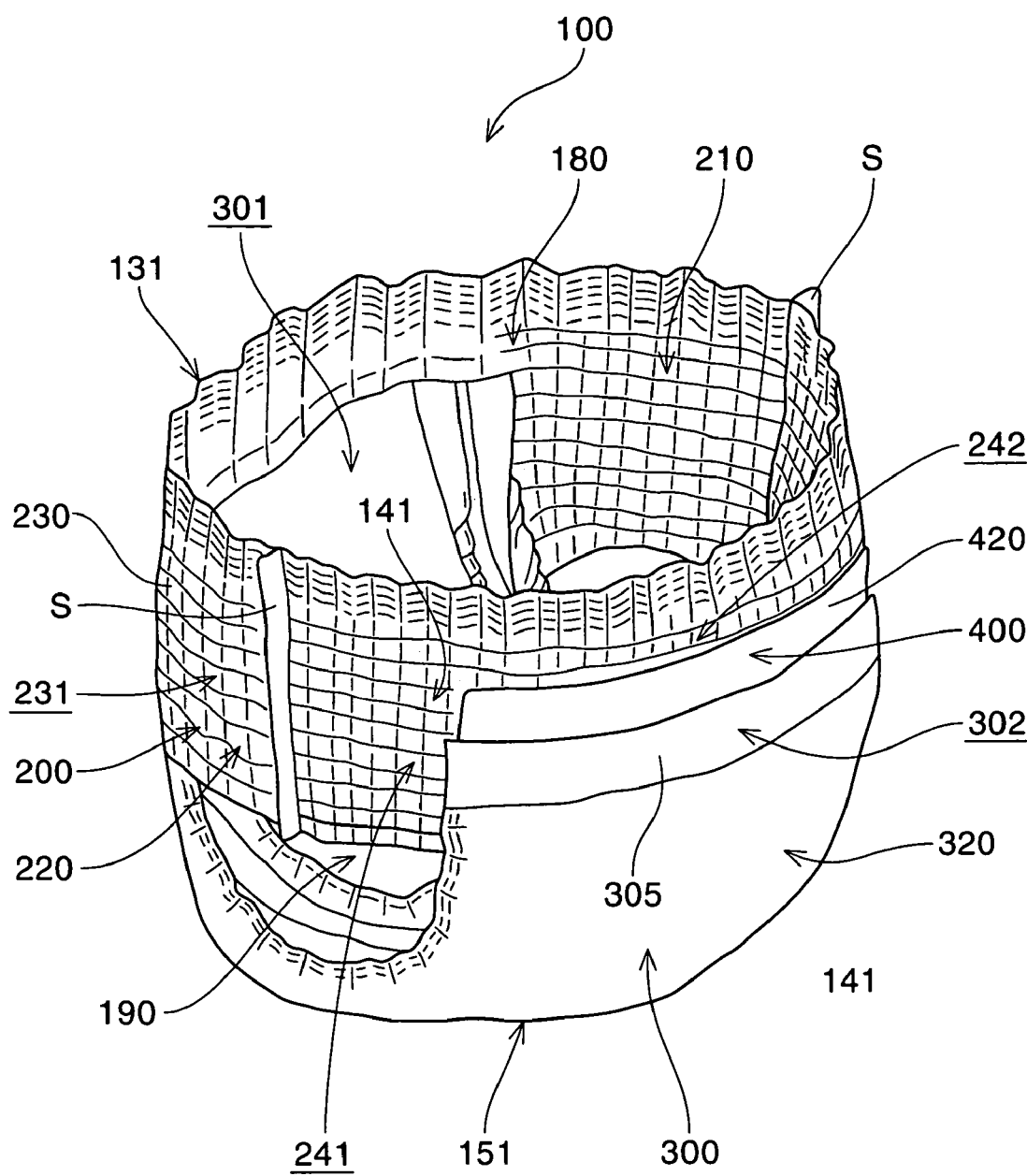
FIG. 5 is a schematic perspective view of the garment illustrated in FIG. 1 when the crotch panel is refastened to the second waist panel.
Figure 9:
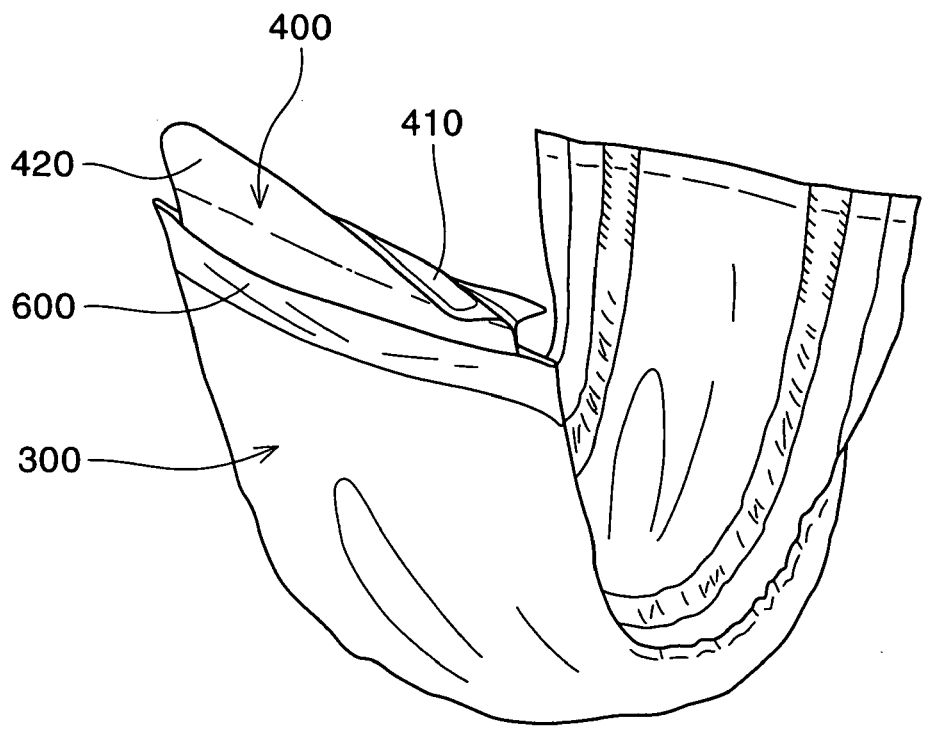
FIG. 9 is a schematic perspective view of the fastening member and the crotch panel before the fastening member is contained into a holder.
Figure 10:
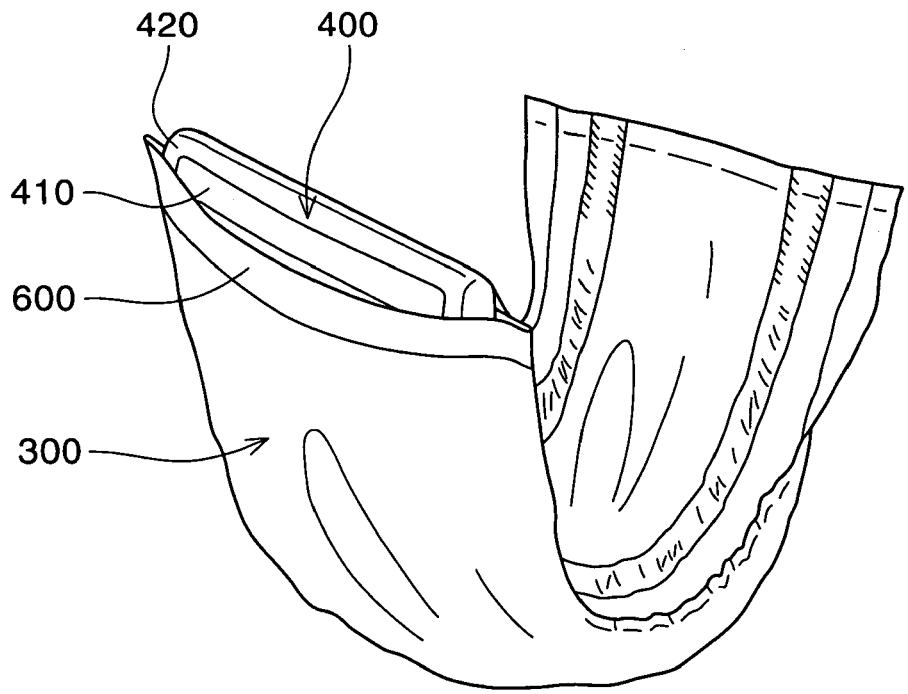
FIG. 10 is a schematic perspective view of the fastening member and the crotch panel when the fastening member is contained into a holder.

As illustrated in FIG. 3, the fastening member 400 is positioned underneath the second waist panel 141 and is not exposed outside of the second waist panel 141 until the releasable joint 500 is released in order to prevent undesirable contamination of the fastening member 400 before use. The fastening member 400 can be exposed by releasing the releasable joint 500 as illustrated in FIG. 4. Subsequently, the garment 100 can be refastened on the wearer's body by engaging the patch 410 of the fastening member 400 with the exterior surface 141B of the second waist panel 141 as illustrated in FIG. 5. Further, the garment 100 may comprise a holder 600 to contain the fastening member 400. As illustrated in FIGS. 7, 9 and 10, the fastening member 400 can be contained into the holder 600 so that the fastening member 400 is not exposed before use and is not fastened to any portion of the second waist panel 141 before the releasable joint 500 is released. In such an embodiment, the fastening member 400 can be protected from undesirable contamination and would not unexpectedly fasten to, e.g., a wearer's clothes when the crotch panel is reclosed through the wearer's legs.

Figure 11:
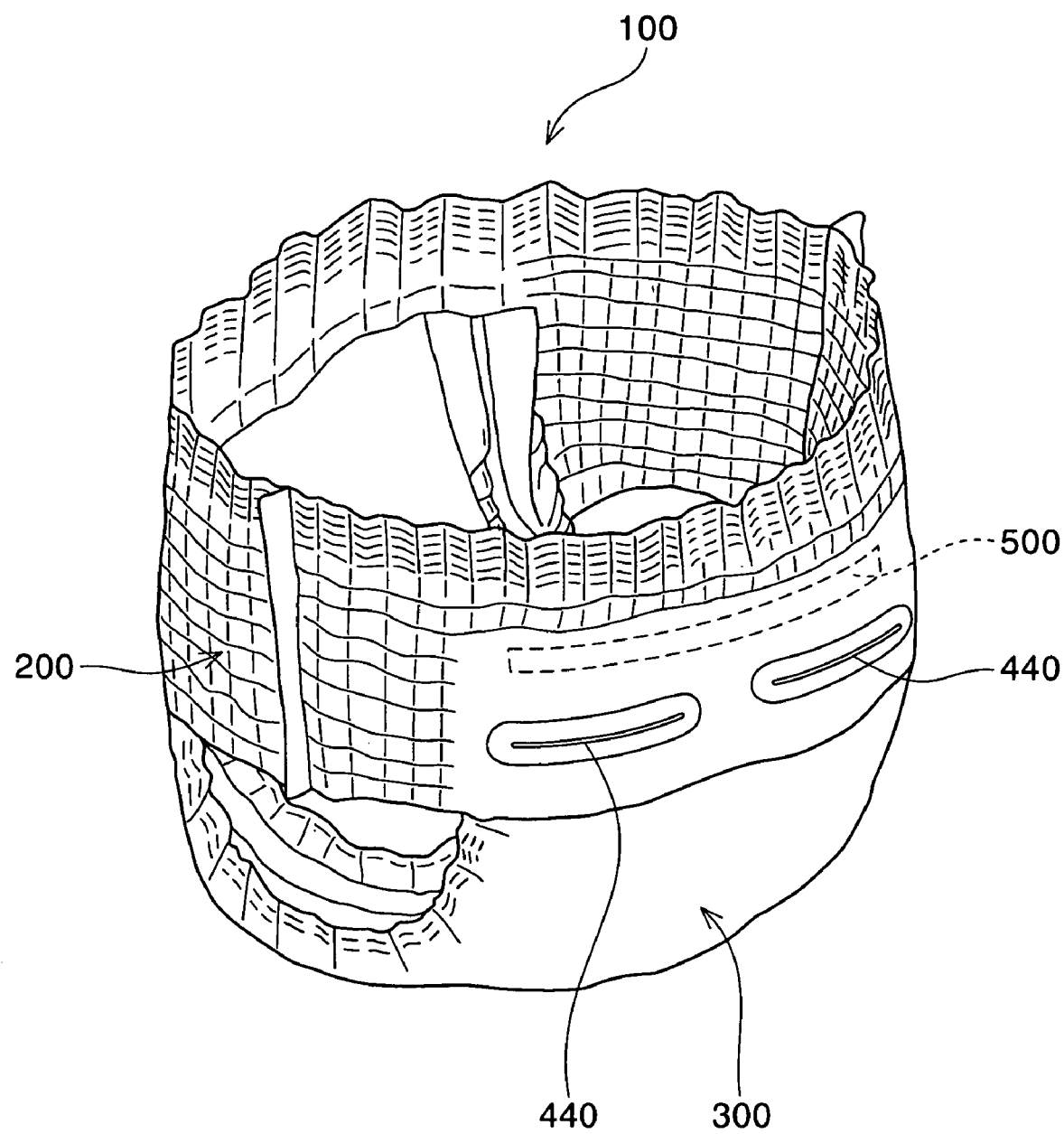
FIG. 11 is a schematic perspective view of another embodiment of a garment of the present invention before the releasable joint is released.
Figure 12:
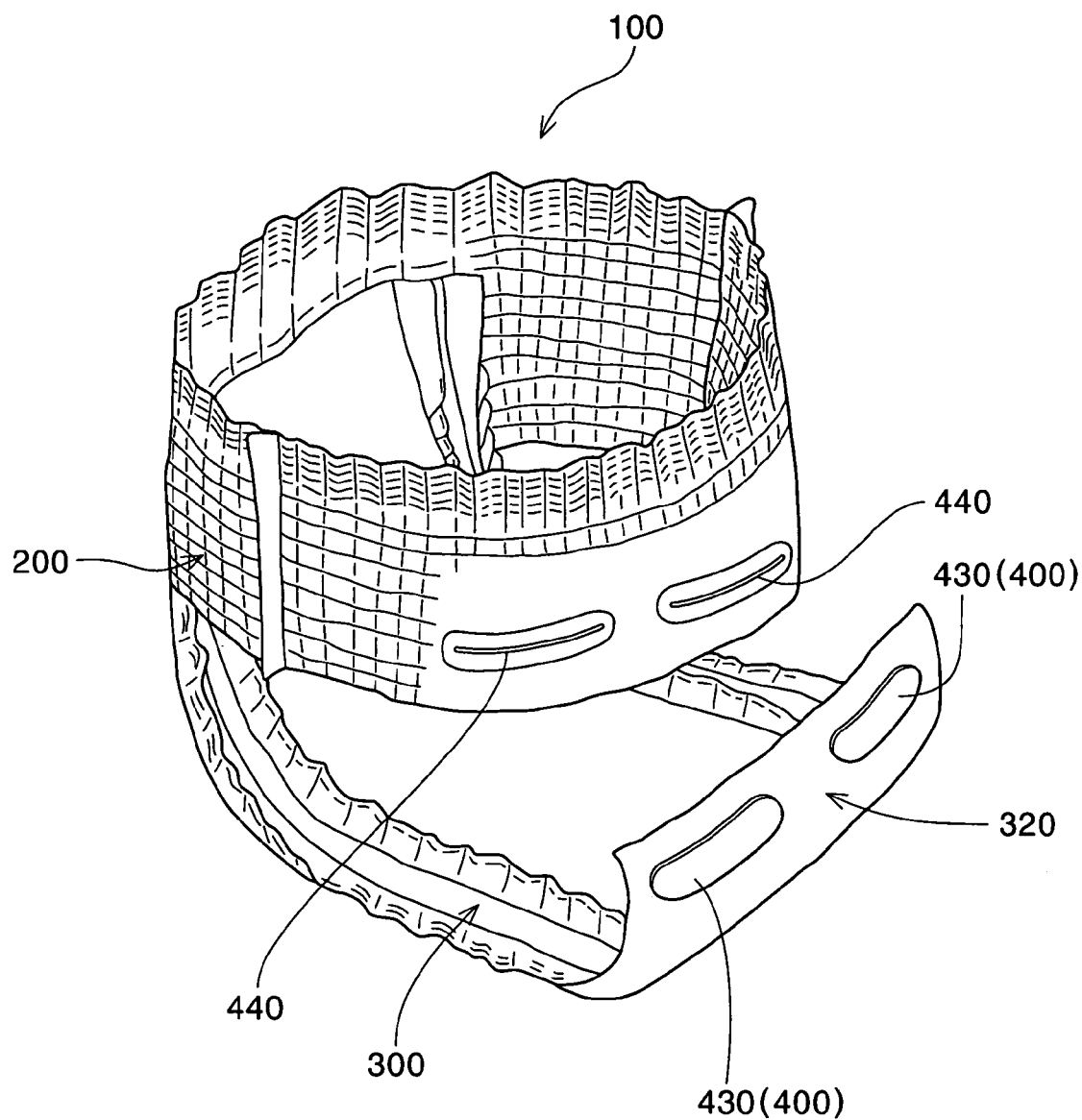
FIG. 12 is a schematic perspective view of the garment illustrated in FIG. 11 after the releasable joint is released.
Figure 13:
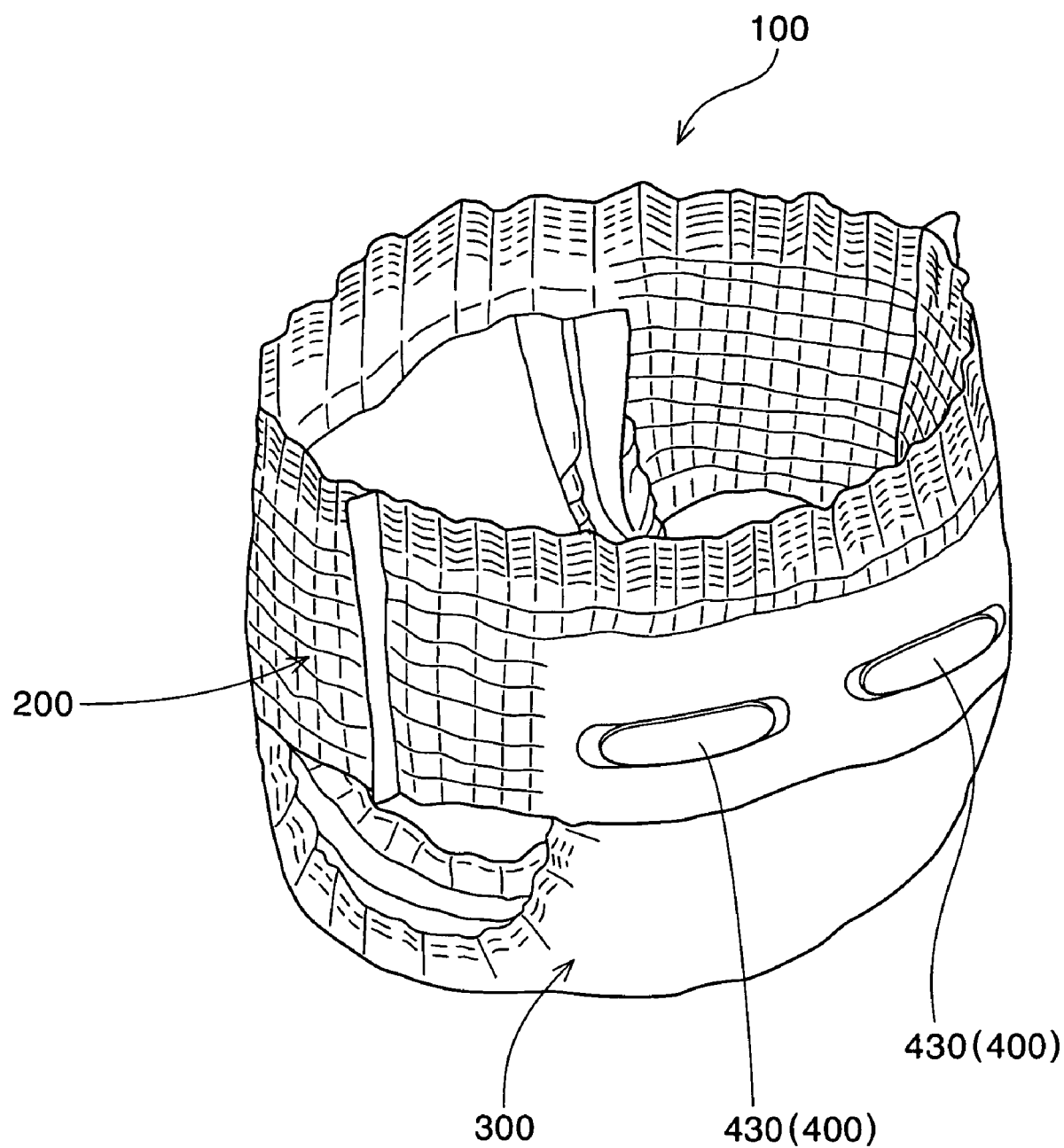
FIG. 13 is a schematic perspective view of the garment illustrated in FIG. 11 when the crotch panel is refastened to the second waist panel.

FIGS. 11 to 13 illustrate another embodiment of the fastening member 400. In the embodiment, the fastening member 400 comprises a tab member 430 fixed to the outer surface 320 of the crotch panel 300. If such a tab member 430 is selected for the fastening member 400, the second waist panel 141 can have a slot portion 440 with which the tab member 430 is releasably and repeatedly engageable. The tab member 430 may be also fixed to the inner surface 310 of the crotch panel 300. On the contrary, the fastening member 400 may have a slot portion if the second waist panel 141 comprises a tab member with which the slot portion is releasably and repeatedly engageable. As illustrated in FIG. 11, the tab member 430 of the fastening member 400 is positioned underneath the second waist panel 141 and is not exposed outside of the second waist panel 141 until the releasable joint 500 is released. The tab member 430 of the fastening member 400 can be exposed by releasing the releasable joint 500 as illustrated in FIG. 12. Subsequently, the garment 100 can be refastened on the wearer's body by passing the tab member 430 through the slot portion 440 as illustrated in FIG. 13. Any other known fastening means e.g., cohesive, magnets, hermaphroditic fasteners, buckles, buttons, clasps or the like, may be also acceptable for the fastening member 400.

Figure 15:
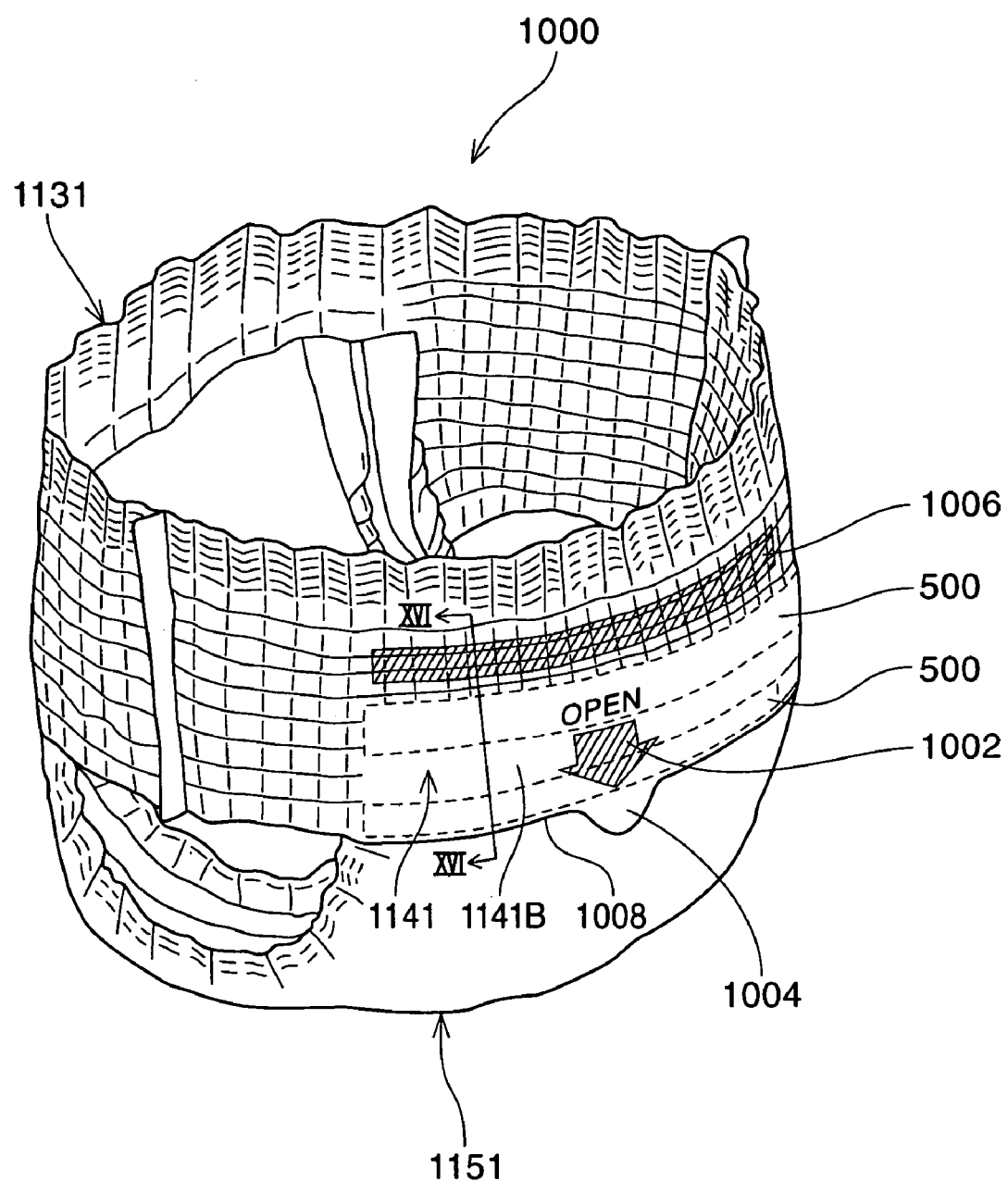
FIG. 15 is a schematic perspective view of alternative embodiment of the garment before the releasable joint is released, and showing the second waist region of the garment.

FIG. 15 illustrates another embodiment of the garment. The garment 1000 comprises a first waist panel 1131, a second waist panel 1141 and a crotch panel 1151. The garment 1000 has an opening indicator 1002 provided on the exterior surface 1141B of the second waist panel 1141 and an opening tab 1004 for facilitating the opening operation. The garment 1000 also has a landing zone indicator 1006 provided on the second waist panel 1141 for fastening the fastening member 1400. Further, in the embodiment shown in FIG. 15, the releasable joint 500 comprises two components; one component extending in the lateral direction along and adjacent the openable end 1305 of the crotch panel 1151 and the other component extending in the lateral direction along and adjacent the lower end 1008 of the second waist panel 1141. The other component of the releasable joint 500 extending along and adjacent the lower end 1008 is positioned in the area where the absorbent core exits when the garment 1000 includes the absorbent core.

Figure 16:
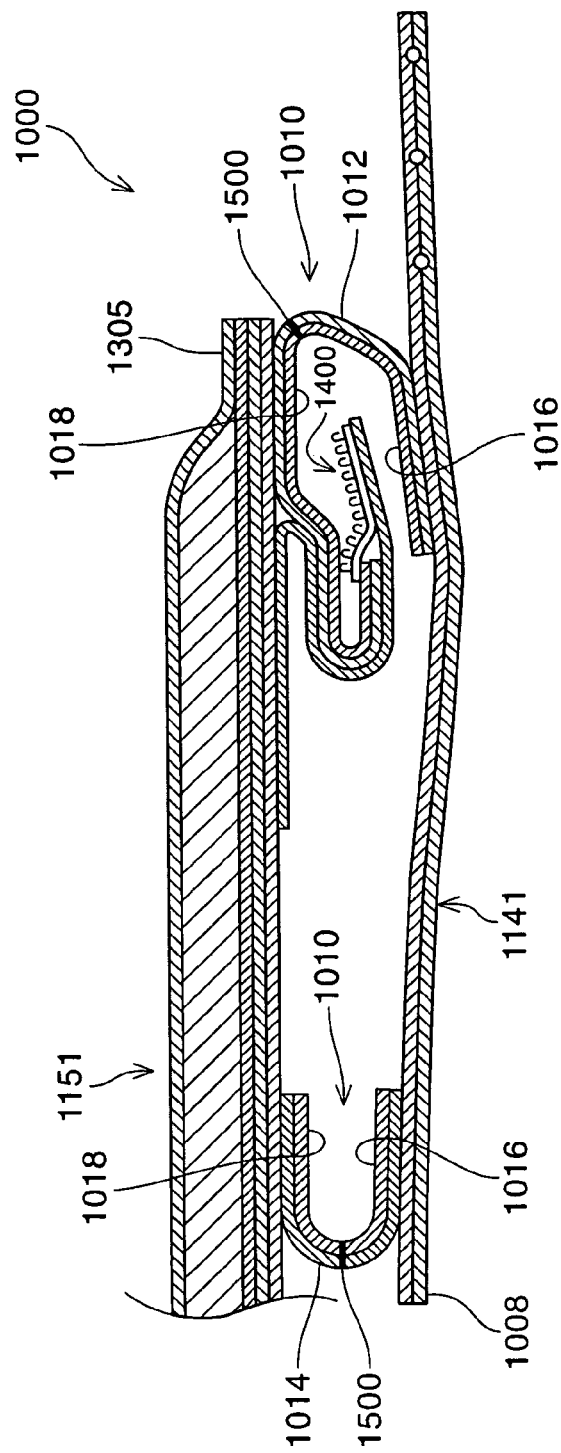
FIG. 16 is a cross-sectional view taken along line XVI-XVI of FIG. 15.
Figure 17:
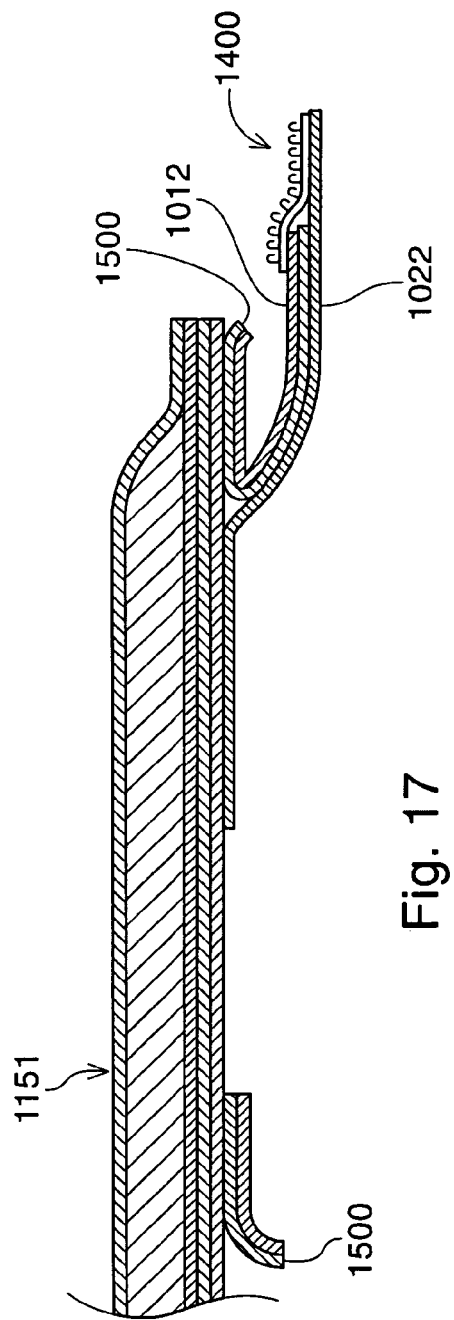
FIG. 17 is a cross-sectional view in which the releasable joint is released and the second waist panel is removed from the configuration shown in FIG. 16.

FIGS. 16 and 17 illustrate another embodiment of the releasable joint. FIG. 16 is a cross-sectional view taken along line XVI-XVI of FIG. 15. The garment 1000 comprises an attachment unit 1010 provided between the second waist panel 1141 and the crotch panel 1151. The attachment unit 1010 comprises a first attachment unit 1012 provided along and adjacent the openable end 1305 of the crotch panel 1151 and a second attachment unit 1014 provided along and adjacent the lower end 1008 of the second waist panel 1141. Both of the first and second attachment units 1012 and 1014 are attached to the second waist panel 1141 at a first permanent attachment portion 1016 and are attached to the crotch panel 1151 at a second permanent attachment portion 1018. The fastening member 1400 is also provided along and adjacent the openable end 1305 of the crotch panel 1151 and joined to the crotch panel 1151. The fastening member 1400 is folded as shown in FIG. 16 until the releasable joint 1500 is released. In order to keep the folding configuration of the fastening member 1400, a portion of the fastening member 1400 may be, for example, provisionally joined to a portion of the attachment unit 1012. The releasable joint 1500 is provided between the first attachment portion 1016 and the second attachment portion 1018 such that the attachment unit 1012, 1014 separates at the releasable joint 1500 when the releasable joint 1500 is released. In the embodiment shown in FIG. 16, the releasable joint 1500 may be formed with perforations formed in the attachment unit 1012, 1014. After the releasable joint 1500 is released, the fastening member 1400 is unfolded to provide a fastening function as shown in FIG. 17.

Figure 18:
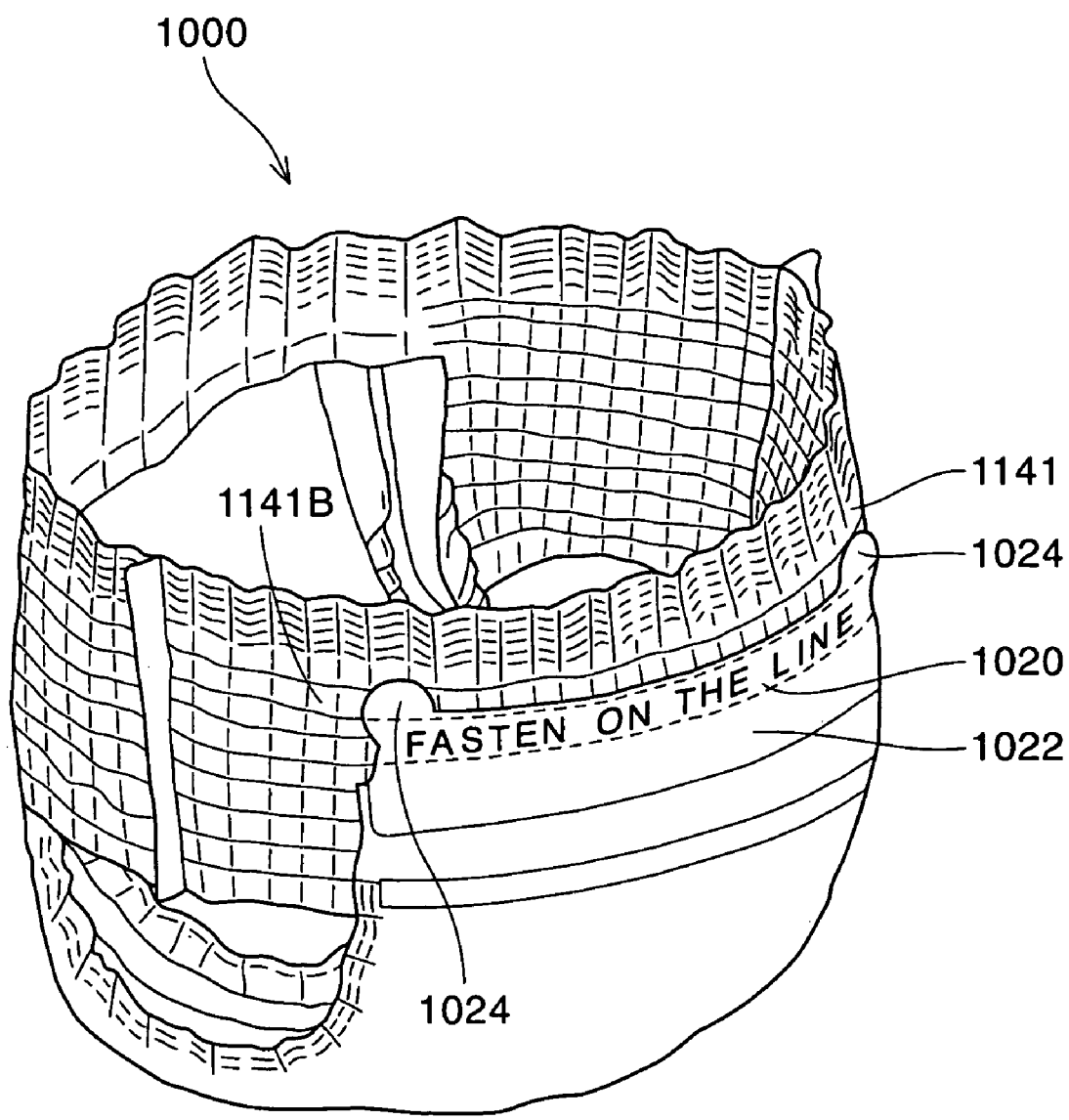
FIG. 18 is a schematic perspective view of alternative embodiment of the garment in which the crotch panel is refastened to the second waist panel.

FIG. 18 illustrates another embodiment of the garment. FIG. 18 shows a configuration of garment where the fastening member 1400 is refastened to the exterior surface 1141B of the second waist panel 1141 to reform the pant shape after the releasable joint 1500 is released. The garment 1000 has an explanatory indicator 1020 on the backside of the substrate 1022 to which the fastening member 1400 is joined (refer to FIG. 17 as well) such that the fastening member 1400 is joined to the landing zone indicator 1006. The substrate 1022 to which the fastening member is joined may also have tabs 1024 to facilitate refastening the fastening member 1400.

Figure 19:
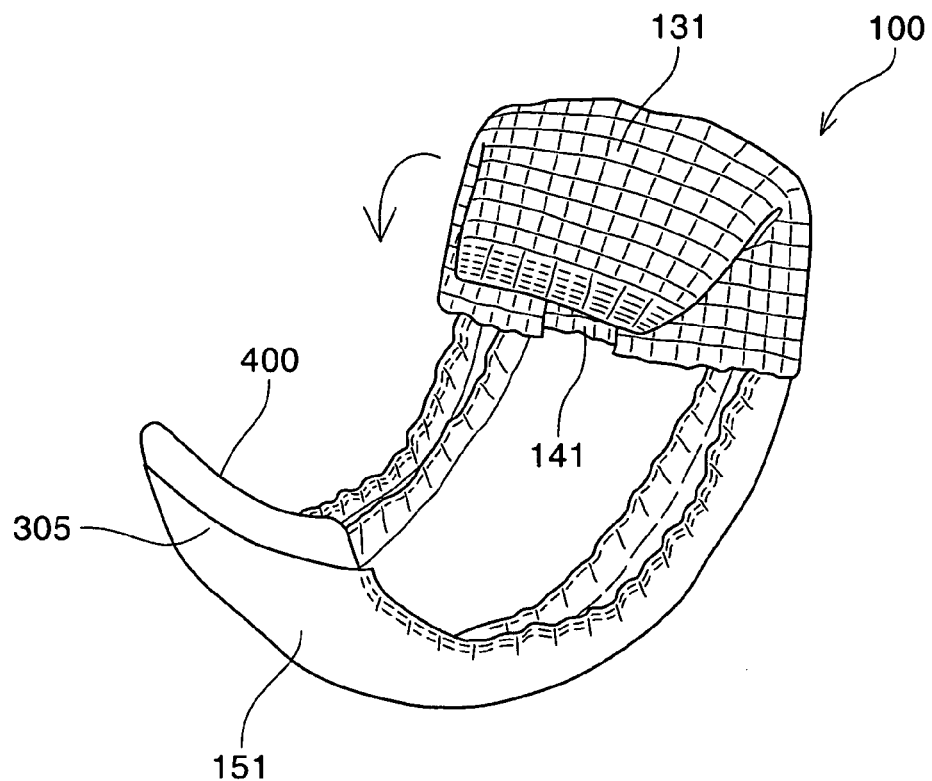
FIG. 19 is a first schematic perspective view showing convenient disposal of the garment.
Figure 20:
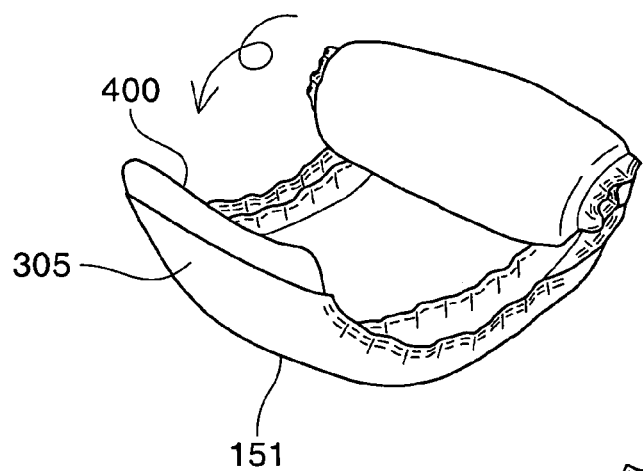
FIG. 20 is a second schematic perspective view showing convenient disposal of the garment.
Figure 21:
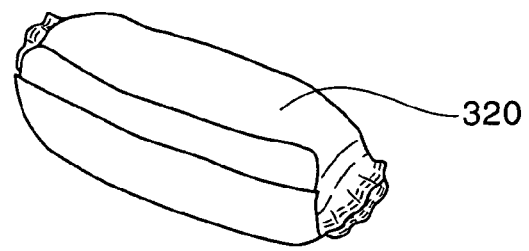
FIG. 21 is a third schematic perspective view showing convenient disposal of the garment.

FIGS. 19 to 21 illustrate convenient disposal of the garment. After the garment 100 is used, the fastening member 400 is released from the second waist panel 141. The first and second waist panels 131, 141 are then folded as shown in FIG. 19 for disposal preparation. After that, the folded first and second waist panels 131, 141 are rolled toward the openable end 305 of the crotch panel 151. The fastening member 400 is then joined to the outer surface 320 of the crotch panel 151 for disposal.

All documents cited in the Detailed Description of the Invention are, are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A pant-type disposable garment having a waist opening and a pair of leg openings, the garments comprising a first waist panel, a second waist panel and a crotch panel positioned between the first waist panel and the second waist panel, the crotch panel being openable and reclosable with respect to at least the second waist panel, and the garment further comprising:
   a releasable joint releasably joining the crotch panel to the second waist panel to preform a pant shape and the releasable joint being released to first open the crotch panel, wherein the releasable joint is provided to join a portion of the second waist panel and a portion of the crotch panel, and
   a fastening member being capable of refastening the crotch panel to the second waist panel to reform the pant shape after the releasable joint is released; and an attachment unit provided between the second waist panel and the crotch panel, the attachment unit is attached to the second waist panel at a first permanent attachment portion and is attached to the crotch panel at a second permanent attachment portion, and the releasable joint is provided between the first permanent attachment portion and the second permanent attachment portion such that the attachment unit separates at the releasable joint when the releasable joint is released.

2. The pant-type disposable garment of claim 1 wherein the first waist panel is a front waist panel and the second waist panel is a rear waist panel.

3. The pant-type disposable garment of claim 1 wherein the first waist panel is a rear waist panel and the second waist panel is a front waist panel.

4. The pant-type disposable garment of claim 1 wherein the crotch panel is openable and reclosable with respect to both of the first waist panel and the second waist panel.

5. The pant-type disposable garment of claim 1 wherein the releasable joint is incapable of joining the crotch panel to the second waist panel once the releasable joint is released.

6. The pant-type disposable garment of claim 1 wherein each of the first waist panel, the second waist panel and the crotch panel comprises a separate member from each other.

7. The pant-type disposable garment of claim 1 wherein the crotch panel has an openable end being openable with respect to the second waist panel.

8. The pant-type disposable garment of claim 7 wherein the crotch panel has a fixed end permanently joined to the first waist panel.

9. The pant-type disposable garment of claim 7 wherein the fastening member is provided on the crotch panel adjacent to the openable end.

10. The pant-type disposable garment of claim 9 wherein the fastening member comprises a hook-type material and the first waist panel comprises a receiving material complementary to the hook-type material.

11. The pant-type disposable garment of claim 3 wherein the fastening member is not exposed outside of the second waist panel before the releasable joint is released.

12. The pant-type disposable garment or claim 11 wherein the fastening member is not fastened to any portion of the second waist panel before the releasable joint is released.

* * * * *